United States Patent
Byeon et al.

(10) Patent No.: US 10,931,880 B2
(45) Date of Patent: Feb. 23, 2021

(54) ELECTRONIC DEVICE AND METHOD FOR PROVIDING INFORMATION THEREOF

(71) Applicant: Samsung Electronics Co., Ltd., Suwon-si (KR)

(72) Inventors: Junok Byeon, Suwon-si (KR); Wongeun Shim, Suwon-si (KR); Kyungtae Kim, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/720,812

(22) Filed: Dec. 19, 2019

(65) Prior Publication Data
US 2020/0204736 A1  Jun. 25, 2020

(30) Foreign Application Priority Data
Dec. 21, 2018  (KR) .......................... 10-2018-0167001

(51) Int. Cl.
| | | |
|---|---|---|
| H04N 5/232 | (2006.01) | |
| A63B 24/00 | (2006.01) | |
| A63B 71/06 | (2006.01) | |

(52) U.S. Cl.
CPC ..... *H04N 5/23299* (2018.08); *A63B 24/0062* (2013.01); *A63B 71/0622* (2013.01);
(Continued)

(58) Field of Classification Search
CPC ............ H04N 5/23299; H04N 5/23203; A63B 24/0062; A63B 71/0622;
(Continued)

(56) References Cited

U.S. PATENT DOCUMENTS

| | | | |
|---|---|---|---|
| 2010/0190610 A1 | 7/2010 | Pryor et al. | |
| 2013/0120445 A1* | 5/2013 | Shimomura | ....... G06K 9/00342 345/629 |

(Continued)

FOREIGN PATENT DOCUMENTS

| | | |
|---|---|---|
| KR | 10-2010-0058031 A | 6/2010 |
| KR | 10-1094648 B1 | 12/2011 |

(Continued)

OTHER PUBLICATIONS

International Search Report dated Apr. 14, 2020, issued in International Application No. PCT/KR2019/018137.
(Continued)

*Primary Examiner* — Nam D Pham
(74) *Attorney, Agent, or Firm* — Jefferson IP Law, LLP

(57) ABSTRACT

An electronic device and a method for providing information thereof are provided. In an embodiment, the electronic device is configured to receive a user input for selecting an exercise through a user interface or a wireless communication circuit, select a guide image corresponding to the selected exercise, analyze the selected guide image, acquire a first image of a user through at least one camera at a first location, determine a second location for the electronic device based at least in part on the analyzed guide image and the acquired first image of the user, control at least one driver to move the electronic device based at least in part on the determined second location, acquire a second image of the user through the at least one camera after a movement of the electronic device, and generate a combined image by combining the selected guide image and the acquired second image of the user.

16 Claims, 17 Drawing Sheets

(52) U.S. Cl.
CPC .. *H04N 5/23203* (2013.01); *A63B 2024/0068* (2013.01); *A63B 2071/0683* (2013.01); *A63B 2220/807* (2013.01); *A63B 2225/50* (2013.01); *A63B 2230/62* (2013.01)

(58) Field of Classification Search
CPC .... A63B 2024/0068; A63B 2071/0683; A63B 2220/807; A63B 2225/50; A63B 2230/62; G06F 3/01; G06F 3/011; G16H 30/40; G16H 40/63; G16H 20/30; G06K 9/00342
See application file for complete search history.

(56) References Cited

U.S. PATENT DOCUMENTS

| | | | |
|---|---|---|---|
| 2015/0099252 | A1 | 4/2015 | Anderson et al. |
| 2018/0064992 | A1 | 3/2018 | Rothman et al. |
| 2019/0077007 | A1* | 3/2019 | Mallinson ............ G05D 1/0274 |

FOREIGN PATENT DOCUMENTS

| | | |
|---|---|---|
| KR | 10-2013-0032764 A | 4/2013 |
| KR | 10-1416282 B1 | 8/2014 |
| KR | 101599149 B1 | 3/2016 |
| KR | 10-2016-0054325 A | 5/2016 |
| KR | 10-2018-0000110 A | 1/2018 |

OTHER PUBLICATIONS

Written Opinion dated Apr. 14, 2020, issued in International Application No. PCT/KR2019/018137.
Partial European Search Report dated Apr. 9, 2020, issued in European Application No. 19218618.7-1115.
Wei Yang et al., "3D Human Pose Estimation in the Wild by Adversarial Learning", CUHK—SenseTime Joint Lab, The Chinese University of Hong Kong, School of Electrical and Information Engineering, The University of Sydney, The Robotics Institute, Carnegie Mellon University, SenseTime Research, Apr. 16, 2018.
Alexander Toshev et al., "DeepPose: Human Pose Estimation via Deep Neural Networks"; IEEE Conference on Computer Vision and Pattern Recognition, 2014; Dec. 2013.
Oe M., Sato T., Yokoya N. (2005) Estimating Camera Position and Posture by Using Feature Landmark Database. In: Kalviainen H., Parkkinen J., Kaarna A. (eds) Image Analysis. SCIA 2005. Lecture Notes in Computer Science, vol. 3540. Springer, Berlin, Heidelberg.
"Simultaneous localization and mapping"; en.wikipedia.org/wiki/Simultaneous_localization_and_mapping; Jan. 20, 2005; retrieved Dec. 2019.
European Search Report dated Jul. 14, 2020; European Appln. No. 19218618.7-1115/3671549.

* cited by examiner

ELECTRONIC DEVICE AND METHOD FOR PROVIDING INFORMATION THEREOF

CROSS-REFERENCE TO RELATED APPLICATION(S)

This application is based on and claims priority under 35 U.S.C. § 119(a) of a Korean patent application number 10-2018-0167001, filed on Dec. 21, 2018, in the Korean Intellectual Property Office, the disclosure of which is incorporated by reference herein in its entirety.

BACKGROUND

1. Field

The disclosure relates to an electronic device and a method of providing information by the same.

2. Description of the Related Art

Electronic devices (for example, mobile terminals, smartphones, or wearable devices) may provide various functions. For example, smart phones may provide not only a basic voice call function but also a short-range wireless communication (for example, Bluetooth, wireless fidelity (Wi-Fi), or Near Field Communication (NFC)) function, a mobile communication ($3^{rd}$ generation (3G), $4^{th}$ generation (4G), or $5^{th}$ generation (5G)) function, a music or video reproduction function, a photography function, or a navigation function.

Meanwhile, as interest in health increases, recent electronic devices provide health services. For example, users may watch images about various exercise methods through electronic devices.

The above information is presented as background information only to assist with an understanding of the disclosure. No determination has been made, and no assertion is made, as to whether any of the above might be applicable as prior art with regard to the disclosure.

SUMMARY

A user may have a difficulty in doing an exercise without any help of an expert. For example, when the user does the exercise with an incorrect posture, there may be something wrong with his/her body and an exercise effect may deteriorate. However, when the user does the exercise alone, the user may have a difficulty in checking whether his/her posture is correct. Accordingly, the user may photograph his/her feature through a camera to check whether his/her posture is correct.

However, since the electronic device photographs the user at a fixed location, the user may have a difficulty in properly photographing a body part which the user desires or his/her posture at a location which the user desires. Further, the user may not recognize whether his/her posture is correct and which part is incorrect even though the user watches the photographed image.

An electronic device according to various embodiments of the disclosure may move to a location designated (or set) by the user or a location that is determined to be suitable for the exercise and perform photographing.

Aspects of the disclosure are to address at least the above-mentioned problems and/or disadvantages and to provide at least the advantages described below. Accordingly, an aspect of the disclosure is to provide both a guide image and an image obtained by photographing the user.

Additional aspects will be set forth in part in the description which follows and, in part, will be apparent from the description, or may be learned by practice of the presented embodiments.

In accordance with an aspect of the disclosure, an electronic device is provided. The electronic device includes a housing, a user interface, at least one camera disposed on the housing, at least one driver connected to or disposed on the housing to move the housing, a wireless communication circuit located within the housing, a memory, and a processor operatively connected to the user interface, the at least one camera, the at least one driver, the wireless communication circuit, and the memory, wherein the memory stores instructions that, when executed by the processor, configure the processor to receive a user input for selecting an exercise through the user interface or the wireless communication circuit, select a guide image corresponding to the selected exercise, analyze the selected guide image, acquire a first image of a user through the at least one camera at a first location, determine a second location for the electronic device based at least in part on the analyzed guide image and the acquired first image of the user, control the at least one driver to move the electronic device based at least in part on the determined second location, acquire a second image of the user through the at least one camera after a movement of the electronic device, and generate a combined image by combining the selected guide image and the acquired second image of the user.

In accordance with another aspect of the disclosure, an electronic device is provided. The electronic device includes a housing, a user interface, at least one camera disposed on the housing, at least one driver connected to or disposed on the housing to move the housing, a wireless communication circuit located within the housing, a memory, and a processor operatively connected to the user interface, the at least one camera, the at least one driver, the wireless communication circuit, and the memory, wherein the memory stores instructions that, when executed by the processor, configure the processor to acquire a first image of a user through the at least one camera at a first location, identify an exercise by analyzing the acquired first image, select a guide image corresponding to the identified exercise, determine a second location for the electronic device based at least in part on the selected guide image and the acquired first image, control the at least one driver to move the electronic device based at least in part on the determined second location, acquire a second image of the user through the at least one camera after a movement of the electronic device, and generate a combined image by combining the selected guide image and the acquired second image of the user.

In accordance with another aspect of the disclosure, an electronic device is provided. The electronic device includes a housing, a processor, and a memory operatively connected to the processor, wherein the memory stores instructions that, when executed by the processor, configure the processor to determine a size of an exercise space based at least in part on a stored space map, determine a type of a setting screen for setting a location or a direction of a camera based at least in part on the determined size of the exercise space, and provide the determined type of the setting screen.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following detailed description taken in conjunction with the accompanying drawings, in which.

Throughout the drawings, it should be noted that like reference numbers are used to depict the same or similar elements, features, and structures.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely examples of the various embodiments. Accordingly, those ordinary skilled in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
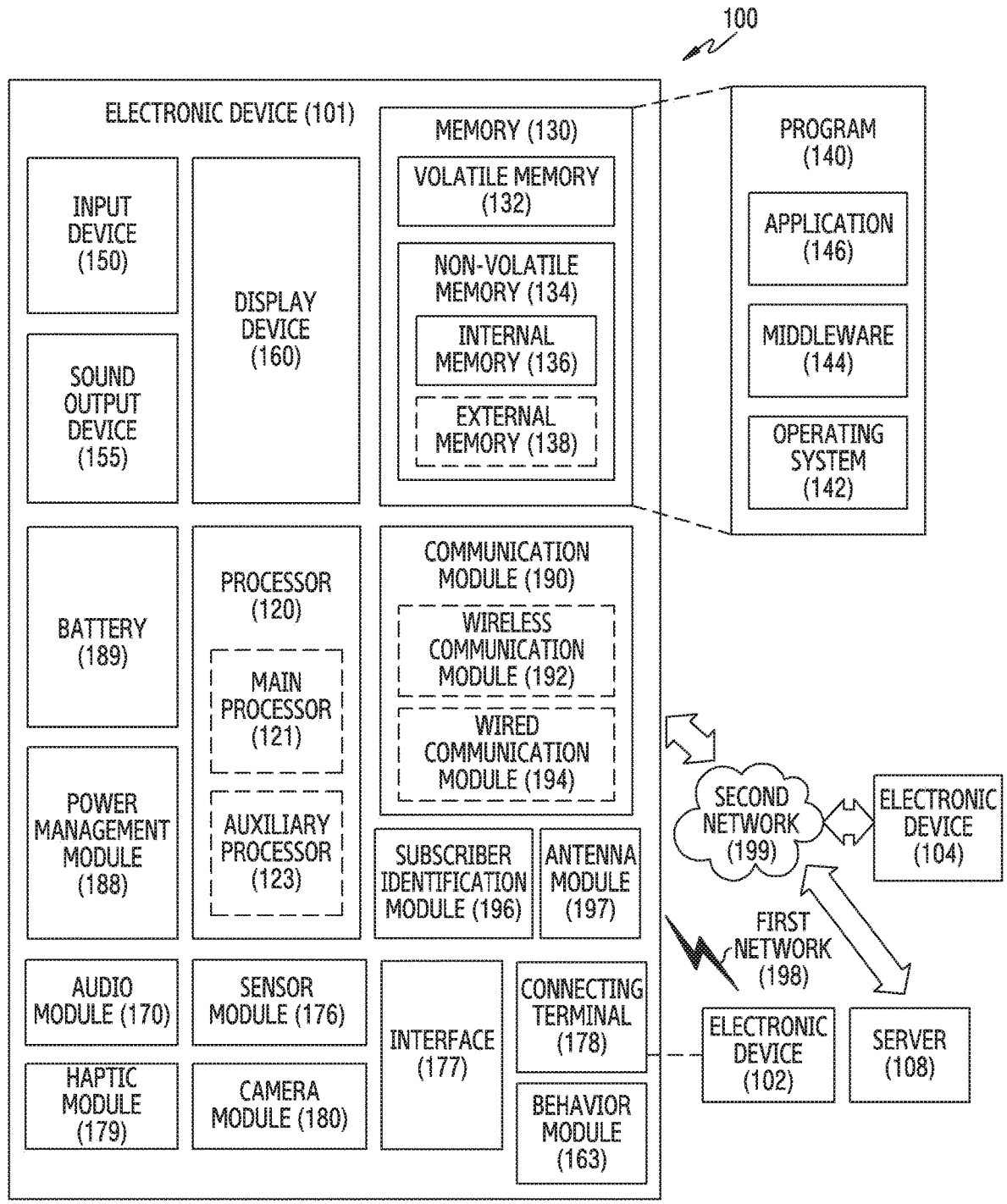
FIG. 1 is a block diagram illustrating an electronic device within a network environment according to an embodiment of the disclosure.

FIG. 1 is a block diagram illustrating an example electronic device 101 in a network environment 100 according to an embodiment of the disclosure.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, a behavior module 163, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an example embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other components (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming call. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The behavior module 163 may express a facial expression change or a posture, or perform a drive. According to an embodiment, the behavior module 163 may include a facial expression motor, a posture expression motor, or a driver. The facial expression motor may visually provide a state of the electronic device 101 through, for example, the display device 160. The driver may be used to, for example, move the electronic device 101 and mechanically change other elements. The driver may rotate in, for example, an up/down direction, left/right direction, or clockwise/counterclockwise direction with respect to at least one axis. The driver may be implemented by combining, for example, a driving motor (for example, a wheel, a spherical wheel, a continuous track, or a propeller) or implemented by independently controlling the same.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an example embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS)

communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the SIM 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., printed circuit board (PCB)). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
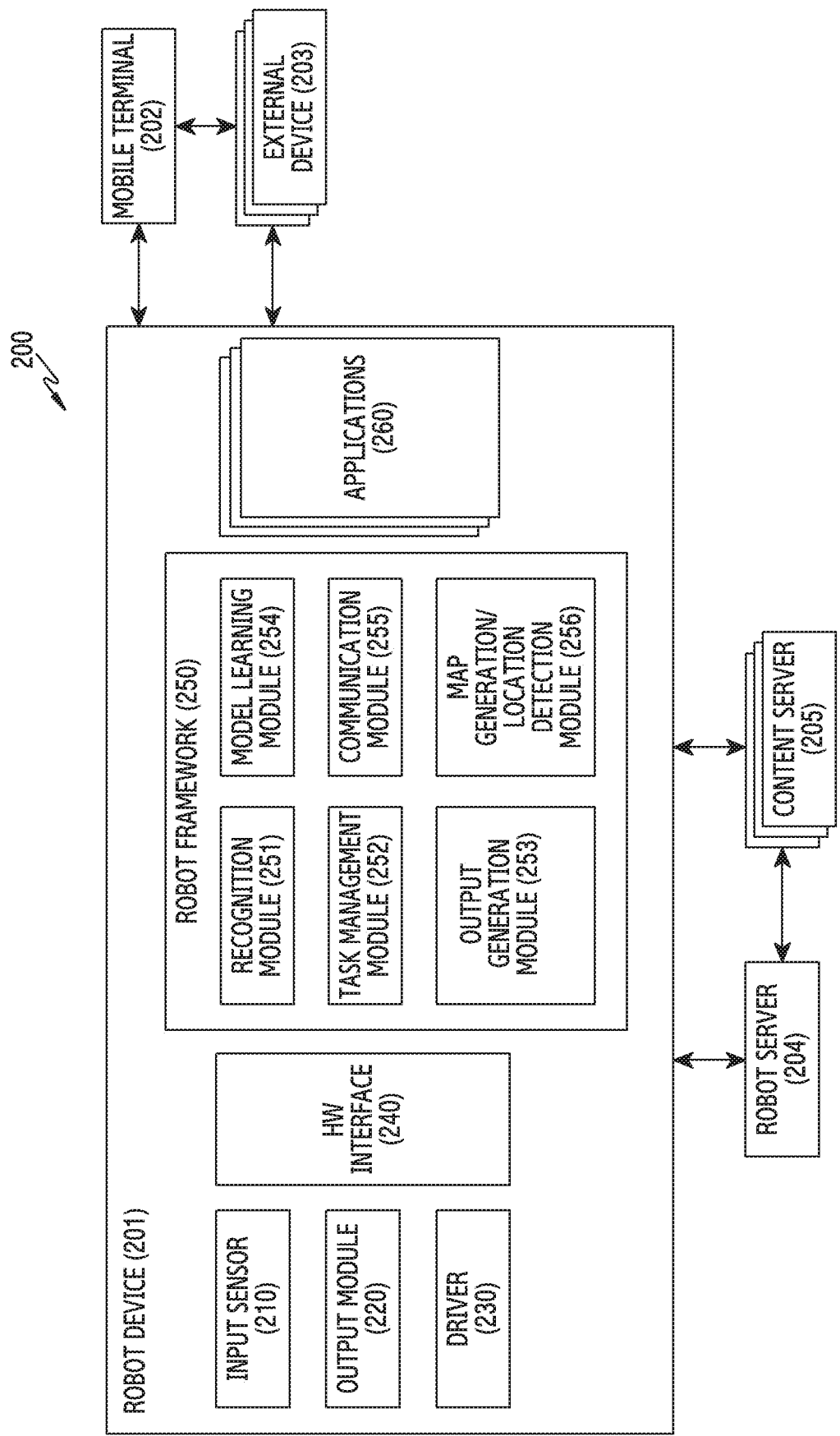
FIG. 2 illustrates the configuration of a system according to an embodiment of the disclosure.

FIG. 2 illustrates the configuration of a system 200 according to an embodiment of the disclosure.

Referring to FIG. 2, the system 200 according to various embodiments of the disclosure may include a robot device 201 (for example, the electronic device 101), a mobile terminal 202 (for example, the electronic device 102), an external device 203, a robot server 204, and a content server 205.

The robot device 201 may be connected to various external devices 203 (for example, a television, a speaker, a home appliance, and an Internet of Things (IoT) device) including the mobile terminal 202 existing in a short range and may use the external devices 203 in order to perform some operations of the applications 260.

In order to support various applications, the robot device 201 may perform (or support) some operations of the robot framework 250 or some operations of the applications 260 through the robot server 204. The robot device 201 may perform some operations of various applications provided to the robot device 201 through the content server 205.

The robot device 201 according to an embodiment may include an input sensor 210, a driver 230, an output module 220, a hardware (HW) interface 240, a robot framework 250, and applications 260.

The input sensor 210 may include various input devices such as a microphone, an image sensor (for example, the camera module 180), a gyro sensor, a gravity sensor, a biometric information sensor, a temperature sensor, a GPS, a touch sensor, a keyboard, a mouse, and a pen. The robot device 201 may receive a user input for selecting at least one exercise through the input sensor 210. For example, the robot device 201 may receive a user voice (for example, a specific exercise name) through the microphone after inquiring the user through the speaker (for example, after outputting an audio signal such as "what exercise program do you want to execute?). Alternatively, the robot device 201 may output an exercise list to the output module 220 (for example, a touch screen display) and receive a user touch input for selecting one exercise. Alternatively, the robot device 201 may output a user interface to the mobile terminal 202 or the external devices 203 connected through communication, and receive a user input from the mobile terminal 202 or the external devices 203.

The input sensor 210 may acquire a user image through the image sensor.

The driver 230 may be connected to or disposed on the housing of the robot device 201 and move the robot device 201. For example, the driver 230 may move the robot device 201 to a photographing location designated or determined according to the exercise.

The output module 220 may include an output device for providing various interfaces to the user such as a display, a speaker, a haptic module, and a light emitting device (LED) except for the driver 230. For example, the output module 220 may output various screens (images) for controlling an exercise program through the display and output an audio signal, a tactile (for example, vibration) signal, or a visual (for example, flickering) signal through the speaker, the haptic module, or the light emitting device (LED).

The hardware (HW) interface 240 may control the input sensor 210, the output module 220, and the driver 230.

The robot framework 250 may provide a platform for the basic operation and service of the robot device 201. The robot framework 250 may include a recognition module 251, a task management module 252, an output generation module 253, a model learning module 254, a communication module 255, and a map generation/location detection module 256.

The recognition module 251 may perform at least one of image recognition (for example, gesture recognition, face recognition, or object tracking) and audio recognition (for example, voice recognition, speaker recognition, wakeup recognition, or acoustic event recognition). According to some embodiments, the recognition module 251 may perform natural language recognition for analyzing a natural language acquired through voice recognition or input through a keyboard.

The recognition module 251 may perform multimodal recognition for generating information required by the robot device 201 using multimodal information including inputs of different modes (for example, a plurality of input devices) acquired through the input sensor 210. According to an embodiment, the recognition module 251 may recognize a sentence spoken by the user on the basis of lip motion information through an image and audio signal information input through the microphone. According to an embodiment, the recognition module 251 may recognize user's emotion on the basis of information obtained by analyzing an image, information obtained by analyzing an audio signal, and context information including location information of the user existing in an image through a statistical method (for example, a neural network, a Convolutional Neural Network (CNN), a Support Vector Machine (SVM), or a Bayes' classifier).

The task management module 252 may plan a task to be performed by the robot device 201 on the basis of information recognized through the recognition module 251, various events generated within the robot device 201, and a task history in the past and perform the planned task.

The output generation module 253 may generate various output signals (for example, an audio signal, a tactile signal, and a visual signal) to be output through the external devices 203 or the mobile terminal 202 included in the robot device 201 or connected to the robot device 201.

The model learning module 254 may include an exercise-specific learning model for classifying (identifying or recognizing) the type of an exercise. The exercise-specific learning model may be data learned using an Artificial Intelligence (AI) algorithm such as machine learning, a neural network, a Convolutional Neural Network (CNN), gene, deep learning, and a classification algorithm (for example, a Support Vector Machine (SVM) or a Bayes' classifier). The model learning module 254 may update the exercise-specific learning module through continuous re-training or adaptation learning.

The communication module 255 may be located within the housing of the robot device 201 and may establish a communication link with the mobile terminal 202, the external devices 203, the robot server 204, and the content server 205. For example, the communication module 255 may receive a user input for selecting at least one exercise from the mobile terminal 202 or the external devices 203. The communication module 255 may transmit a user image and/or a guide image acquired through the image sensor to the external devices 203.

The map generation/location detection module 256 may perform an operation for allowing the robot device 201 to recognize a space through an algorithm such as a Simultaneous Localization and Mapping (SLAM) and to recognize the location of the robot device 201 in the recognized space. The map generation/location detection module 256 may use information acquired through the input sensor 210 or some operations of the recognition module 251. When a target location (for example, the photographing location) is designated or determined, the map generation/location detection module 256 may perform an operation for calculating a path from the current location to the target location and controlling the driver 230 to move to the target location on the basis of the calculated path.

The applications 260 include applications at an end point to be provided to the user by the robot device 201. For example, the applications 260 may include an application for guiding an exercise (exercise guide application). The exercise guide application is described with reference to FIG. 3.

Figure 3:
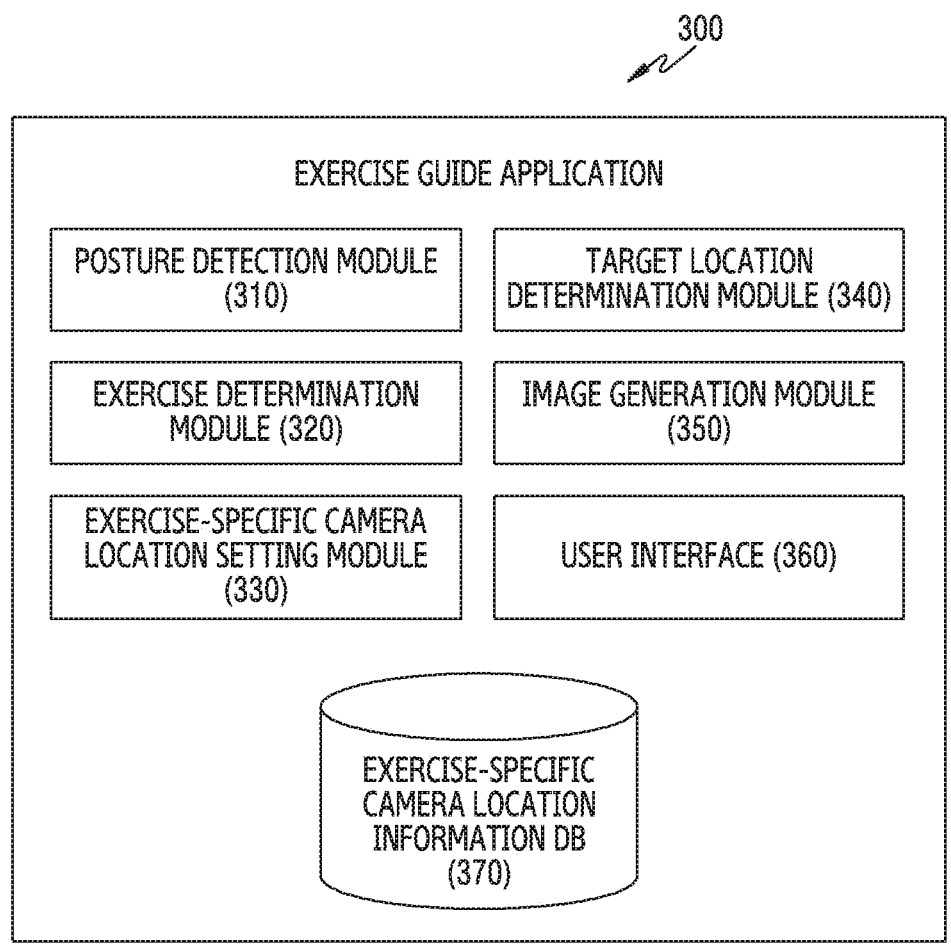
FIG. 3 is a block diagram illustrating an exercise guide application according to an embodiment of the disclosure.

FIG. 3 is a block diagram illustrating an exercise guide application according to an embodiment of the disclosure.

Referring to FIG. 3, an exercise guide application according to an embodiment of the disclosure may include a posture detection module 310, an exercise determination module 320, an exercise-specific camera location setting module 330, a target location determination module 340, an image generation module 350, a user interface 360, and an exercise-specific camera location information database (DB) 370.

The posture detection module 310 may analyze an image stored or acquired through the camera to recognize a person (for example, a user) within the image and determine a posture of the recognized user. For example, the posture detection module 310 may detect which direction the user faces and whether the user takes a specific posture (for example, a standing/lying/sitting/lying flat posture). The user posture may be determined on the basis of skeleton information including at least some of the left hand, right hand, left shoulder, right shoulder, left foot, right foot, pelvis, head, and neck coordinates on the basis of the image analysis result. For example, a vector perpendicular to the plane formed by left shoulder, right shoulder, and pelvis points of the user may be the direction which the user faces. The user posture may be detected three-dimensionally. The user posture may be detected using various algorithms widely known in the technical field of the disclosure.

The exercise determination module 320 may analyze a user image (first image) acquired through the camera by using a classification module (for example, a neural network, an SVM, or a Bayes' classifier) and determine (identify or recognize) which exercise the user is doing. The exercise determination module 320 may determine the type of the exercise with reference to the exercise-specific learning model.

The exercise-specific camera location setting module 330 may control an operation in which the user sets a photographing location (for example, a body part of the user or a viewing angle) of the robot device (for example, the robot device 201) for each exercise. A detailed description thereof will be made with reference to FIGS. 12 to 15.

The exercise-specific camera location information DB 370 may store location information set by the exercise-specific camera location setting module 330.

The target location determination module 340 may determine a target location (for example, a photographing location) to which the robot device moves while the exercise guide application 300 is executed. The target location determination module 340 may determine a space in which the exercise is conducted and calculate a location at which the user who is doing the exercise is photographed. For example, the target location determination module 340 may calculate the location at which the user who is doing the exercise is photographed on the basis of information calculated by the posture detection module 310, information calculated by the exercise determination module 320, and/or location information set by the exercise-specific camera location setting module 330.

The image generation module 350 may generate an image to be provided to the user while the exercise guide application 300 is executed. For example, the image generation module 350 may combine a user image (second image) acquired through the camera at the target location and a guide image of the currently conducted exercise. The image generation module 350 may output the combined image through an output device included in the robot device or an external device connected to the robot device.

The user interface 360 may output various screens for the exercise guide and receive a user input. For example, the user interface 360 may output an exercise list which can be provided by the robot device and receive an input for selecting an exercise to be conducted from the user.

Figure 4:
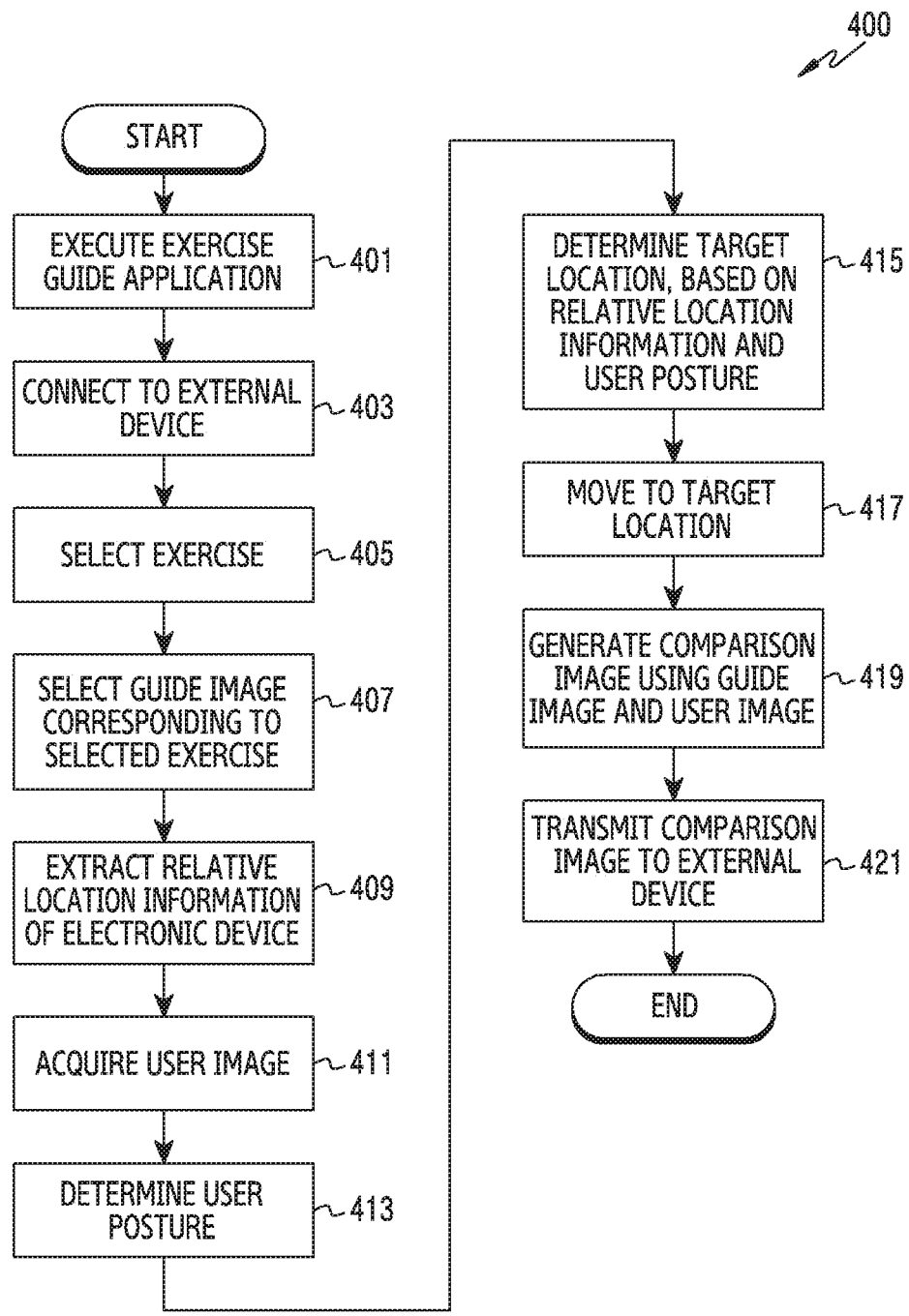
FIG. 4 is a flowchart illustrating a method by which the electronic device provides exercise guide information according to an embodiment of the disclosure.
Figure 5:
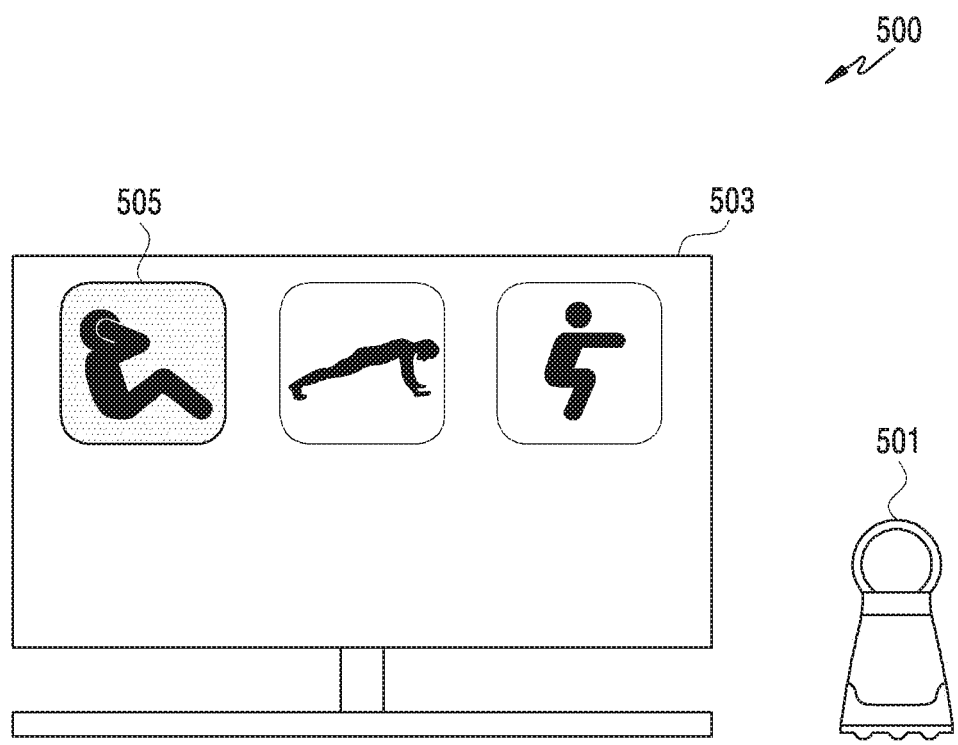
FIG. 5 illustrates an example in which the electronic device provides exercise guide information according to an embodiment of the disclosure.
Figure 6:
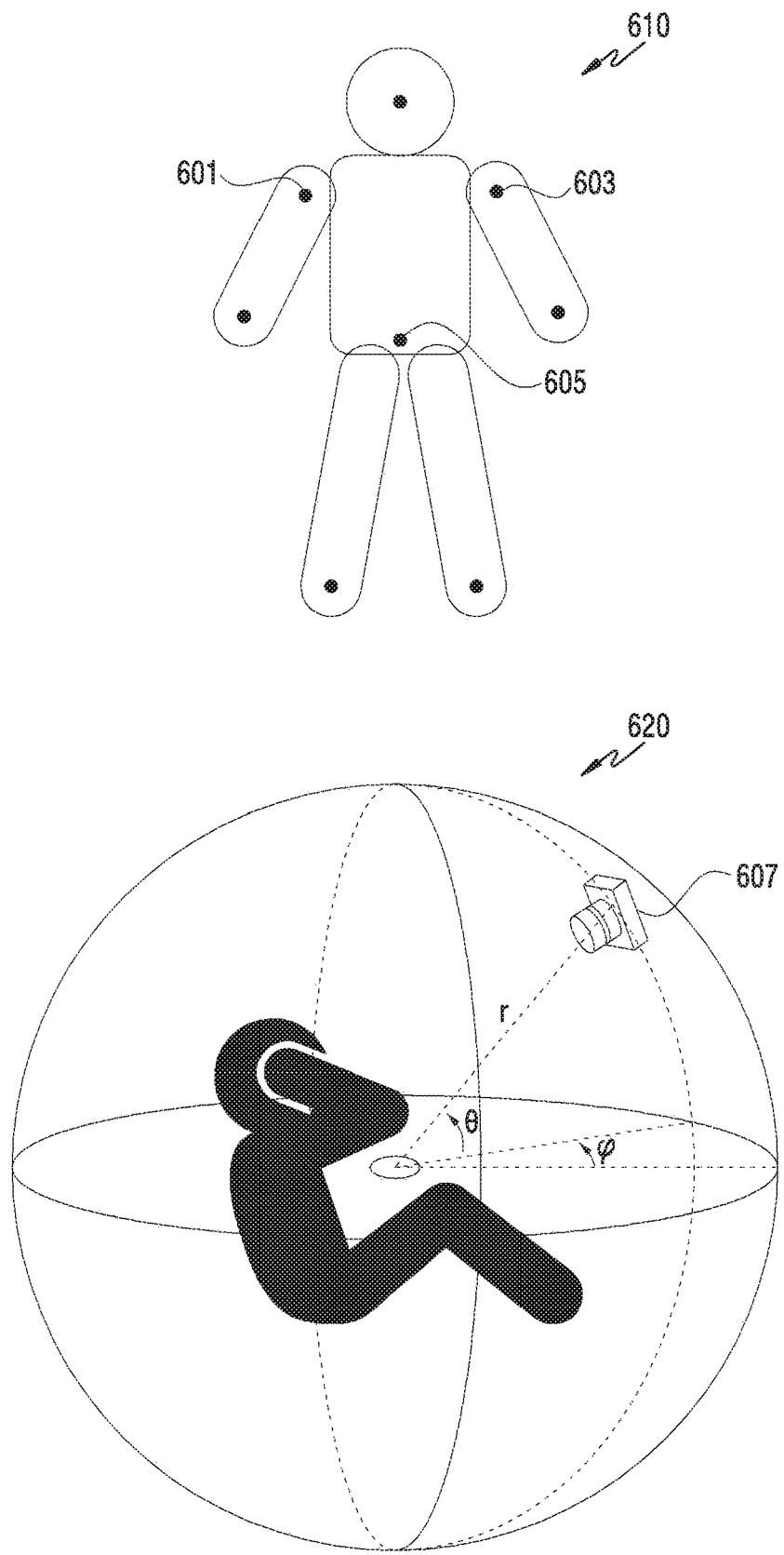
FIG. 6 illustrates an example in which the electronic device provides exercise guide information according to an embodiment of the disclosure.
Figure 7:
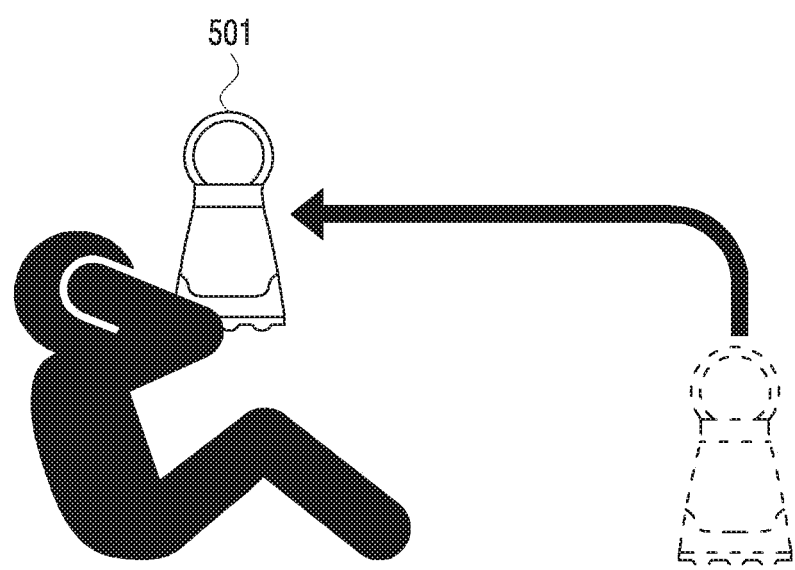
FIG. 7 illustrates an example in which the electronic device provides exercise guide information according to an embodiment of the disclosure.
Figure 8:
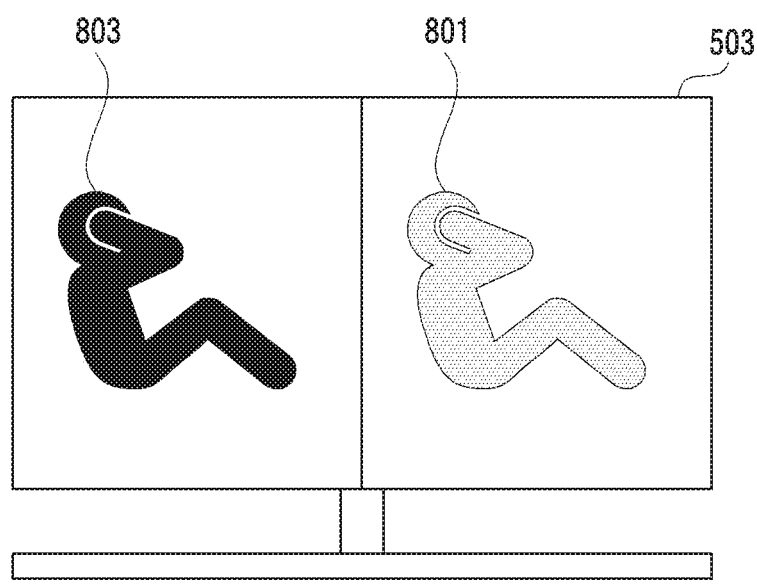
FIG. 8 illustrates an example in which the electronic device provides exercise guide information according to an embodiment of the disclosure.

FIG. 4 is a flowchart 400 illustrating a method by which the electronic device provides exercise guide information according to an embodiment of the disclosure, FIG. 5 illustrates an example in which the electronic device provides exercise guide information according to an embodiment of the disclosure, FIG. 6 illustrates an example in which the electronic device provides exercise guide information according to an embodiment of the disclosure, FIG. 7 illustrates an example in which the electronic device provides exercise guide information according to an embodiment of the disclosure, and FIG. 8 illustrates an example in which the electronic device provides exercise guide information according to an embodiment of the disclosure.

Referring to FIGS. 4 to 8, a processor (for example, the processor 120) of an electronic device (for example, the electronic device 101 or the robot device 201) according to various embodiments of the disclosure may execute an exercise guide application (for example, the exercise guide application 300) in operation 401. For example, the processor may execute the exercise guide application in response to a user input in various types (for example, a touch, a button, and a voice command) Alternatively, the exercise guide application may be executed by a mobile terminal (for example, the mobile terminal 202) connected to the robot device 201.

The processor according to an embodiment of the disclosure may be connected to an external device (for example, a television (TV), a projector, or a hologram device) in operation 403. The electronic device may be connected to the external device through a wireless communication module (circuit) (for example, Bluetooth, Wi-Fi, or Wi-Fi Direct). The external device is a device for providing exercise guide information and may be located in a place where the user easily watches (for example, in front of the user) during the exercise. According to some embodiments, the processor may identify the current location of the electronic device, and when the electronic device is positioned in a place different from the external device, control a driver (for example, the driver 230) to move to the place in which the external device is located on the basis of previously stored space map data. The space map data may be stored data obtained by mapping locations of external devices to a map.

Referring to FIG. 5, the processor according to an embodiment of the disclosure may detect selection of an exercise in operation 405. For example, as indicated by reference numeral 500 of FIG. 5, when the robot device 501 is connected to an external device 503, the robot device 501 may transmit information on exercises which can be conducted (for example, an exercise list) to the external device 503 and receive a user input for selecting a sit-up exercise 505 from the external device 503.

According to some embodiments, the processor may receive a user input for selecting at least one exercise through a user interface (for example, a touch screen, a button, or a microphone) of the electronic device. For example, the processor may output an audio signal for inquiring about which exercise is selected through the speaker, receive a user voice through the microphone, and recognize an exercise selected by the user through voice recognition of the received voice data.

The processor according to an embodiment of the disclosure may select a guide image corresponding to the selected exercise in operation 407. The guide image may be an image of an expert doing an exercise with correct posture. The guide image may be previously downloaded for each exercise and stored in the electronic device, and received by the electronic device from an external server (for example, the content server 205) when an exercise is selected.

The processor according to an embodiment of the disclosure may extract relative location information of the electronic device in operation 409. The relative location information of the electronic device may be previously set for each exercise by the user and stored in the exercise-specific camera location information DB 370.

Referring to FIG. 6, the processor according to an embodiment of the disclosure may acquire a user image (hereinafter, a first image) through the camera in operation 411, and determine a user posture in operation 413. For example, the processor (or the posture detection module 310) may determine a user in the first image and determine posture information. The posture information may include a direction which the user faces and a posture such as standing/sitting/lying/lying flat. The user posture may be determined on the basis of skeleton information of the image-analyzed result. For example, as indicated by reference numeral 610 of FIG. 6, a direction of a vector perpendicular to the plane formed by a user left shoulder 601, a right shoulder 603, and a pelvis point 605 may be the direction which the user faces.

The processor according to an embodiment of the disclosure may determine a target location on the basis of at least some of relative location information and user posture information in operation 415. The relative location information 607 may be expressed by a spherical coordinate system having a distance (r) from the origin, an angle of altitude ($\theta$), and an azimuth ($\varphi$) as indicated by reference numeral 620 of FIG. 6.

When the relative location information 607 includes an azimuth ($\varphi$) of 300 degrees and an angle of altitude ($\theta$) of 45 degrees, and the direction which the user faces determined in operation 413 is 200 degrees, the processor (or the target location determination module 340) may determine 320 degrees (=300+200−180) as the target location (hereinafter, referred to as a first target location).

According to some embodiments, the processor (or the target location determination module 340) may calculate a distance of an occupation ratio (for example, 70%) of the user of a predetermined range in the first image and determine that the calculated distance is a target location (hereinafter, referred to as a second target location).

Referring to FIG. 7, the processor according to an embodiment of the disclosure may move the electronic device to a target location (for example, referred to as a second target location) in operation 417. For example, the processor may move the robot device 501 from the front of the user to the second target location (for example, a left side of the user) by controlling the driver.

According to some embodiments, when the relative location information includes the angle of altitude (θ), the processor may control the height of the camera in accordance with altitude information. To this end, the electronic device may be configured to have the housing including the camera, the height of at least a portion the housing being adjustable.

The processor according to an embodiment of the disclosure may generate a comparison image on the basis of the guide image and the user image (hereinafter, referred to as the second image) acquired at the target location in operation 419 and transmit the generated comparison image to the external device in operation 421. For example, the processor may generate the comparison image by combining the guide image and the second image. The external device 503 receiving the comparison image may output a guide image 801 and a second image 803 as illustrated in FIG. 8.

Referring to FIG. 8, it illustrates that the guide image 801 and the second image 803 are displayed in a split-screen manner, but the images may be displayed in various ways. For example, the guide image 801 and the second image 803 may be displayed in an overlay manner.

Figure 9:
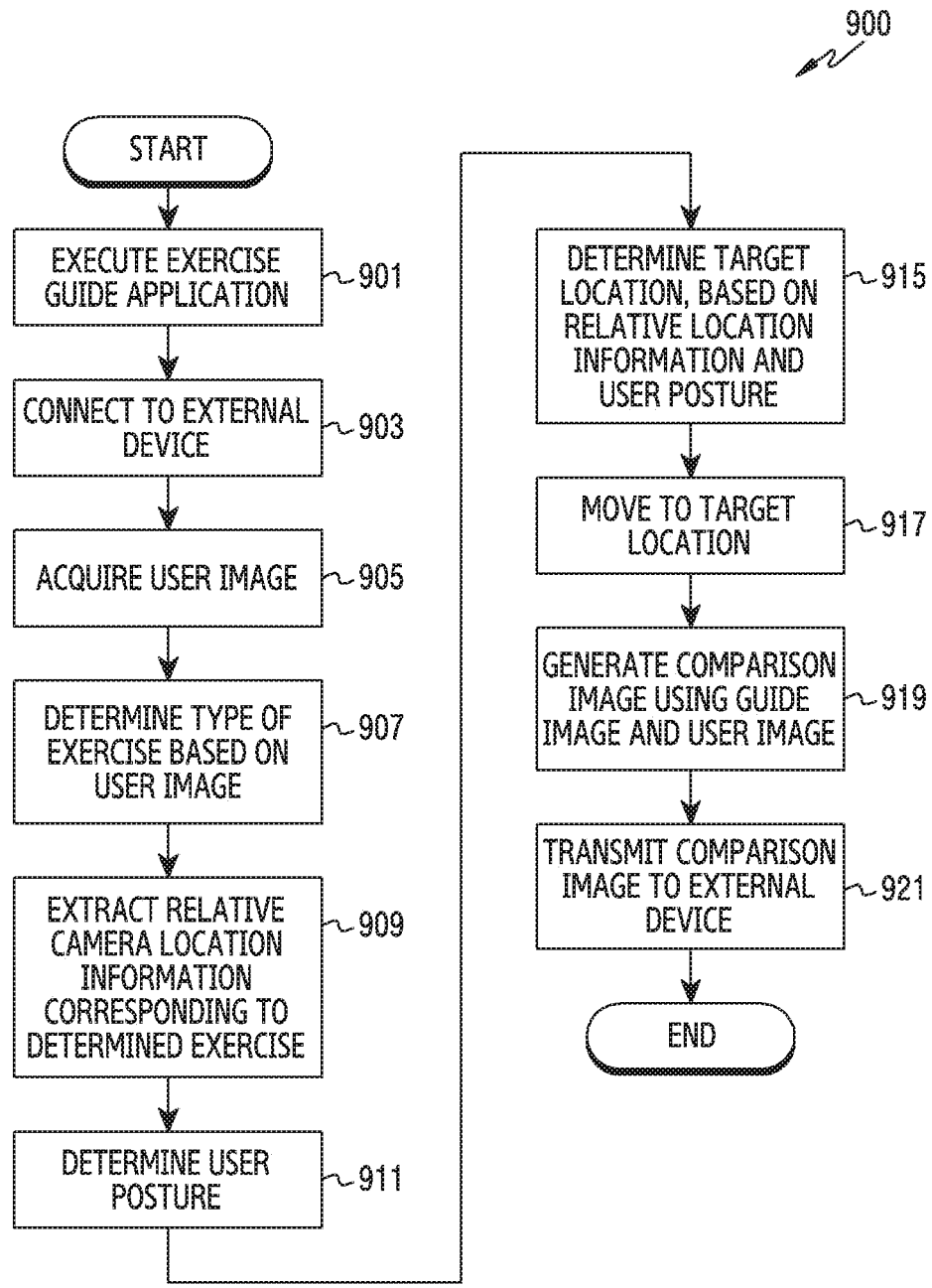
FIG. 9 is a flowchart illustrating a method by which the electronic device provides exercise guide information according to an embodiment of the disclosure.

FIG. 9 is a flowchart 900 illustrating a method by which the electronic device provides exercise guide information according to an embodiment of the disclosure.

Referring to FIG. 9, a processor (for example, the processor 120) of an electronic device (for example, the electronic device 101 or the robot device 201) according to an embodiment of the disclosure may execute an exercise guide application (for example, the exercise guide application 300) in operation 901 and may be connected to an external device (for example, a TV, a projector, or a hologram device) in operation 903.

The processor according to an embodiment of the disclosure may acquire a user image in operation 905. For example, the processor may acquire a user image (hereinafter, referred to as a first image) through a camera.

The processor according to an embodiment of the disclosure may determine (identify or recognize) the type of an exercise on the basis of the acquired image (the first image) in operation 907. For example, the processor (or the exercise determination module 320) may analyze the first image acquired through the camera by using a classification module (for example, a neural network, a Hidden Markov Model (HMM), an SVM, vector quantization, or a Bayes' classifier) and determine (identify or recognize) which exercise is being conducted by the user. The processor (or the exercise determination module 320) may determine the type of the exercise with reference to an exercise-specific learning model.

The processor according to an embodiment of the disclosure may extract relative location information of the electronic device corresponding to the determined exercise in operation 909. The relative location information of the electronic device may be previously set for each exercise by the user and stored in the exercise-specific camera location information DB 370.

When the relative location information of the electronic device is extracted, the processor may perform operations 911, 915, 917, 919, and 921. Operations 911, 915, 917, 919, and 921 of FIG. 9 are similar to operations 413, 415, 417, 419, and 421 of FIG. 4. A detailed description thereof is omitted.

Figure 10:
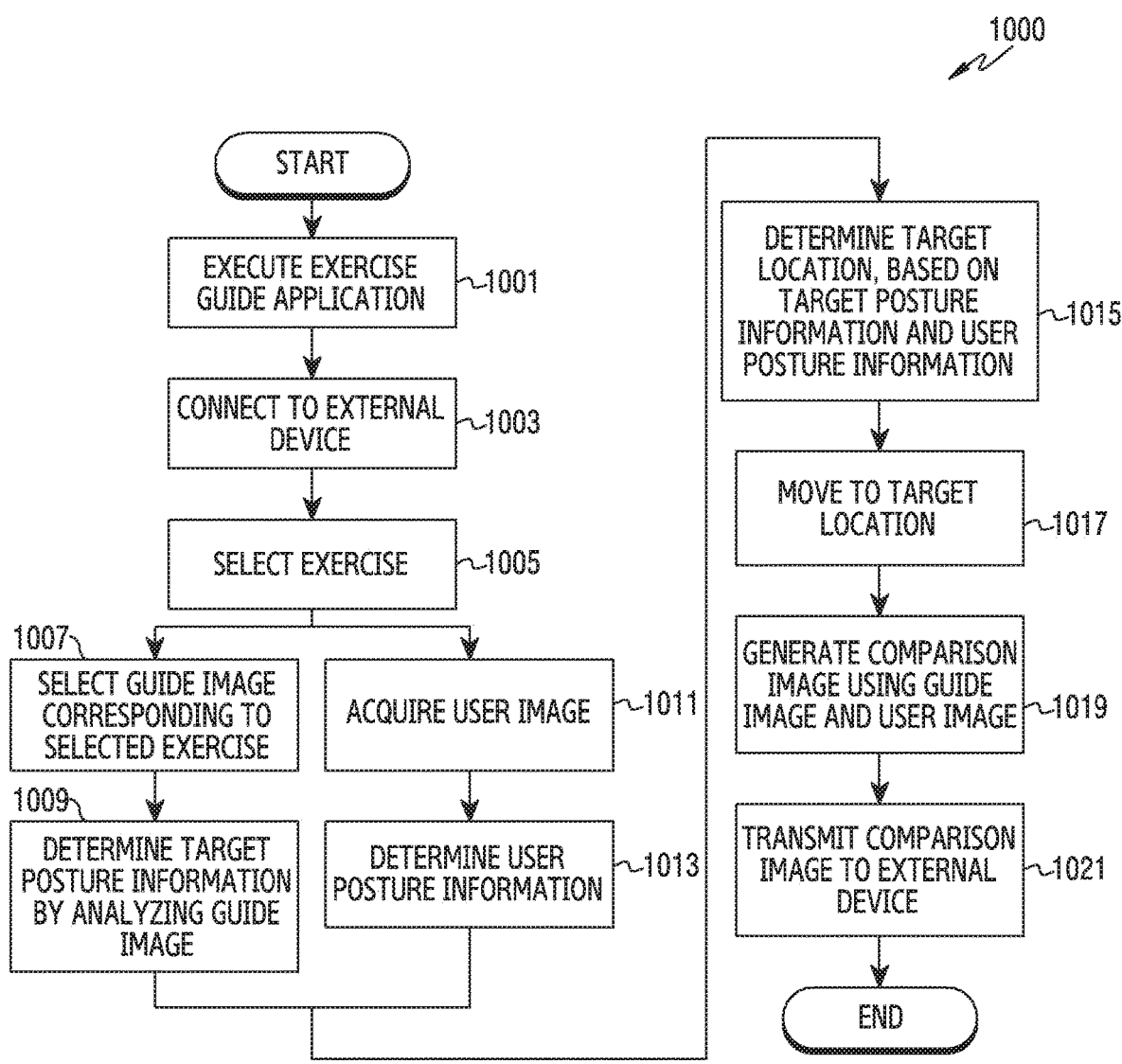
FIG. 10 is a flowchart illustrating a method by which the electronic device provides exercise guide information according to an embodiment of the disclosure.
Figure 11:
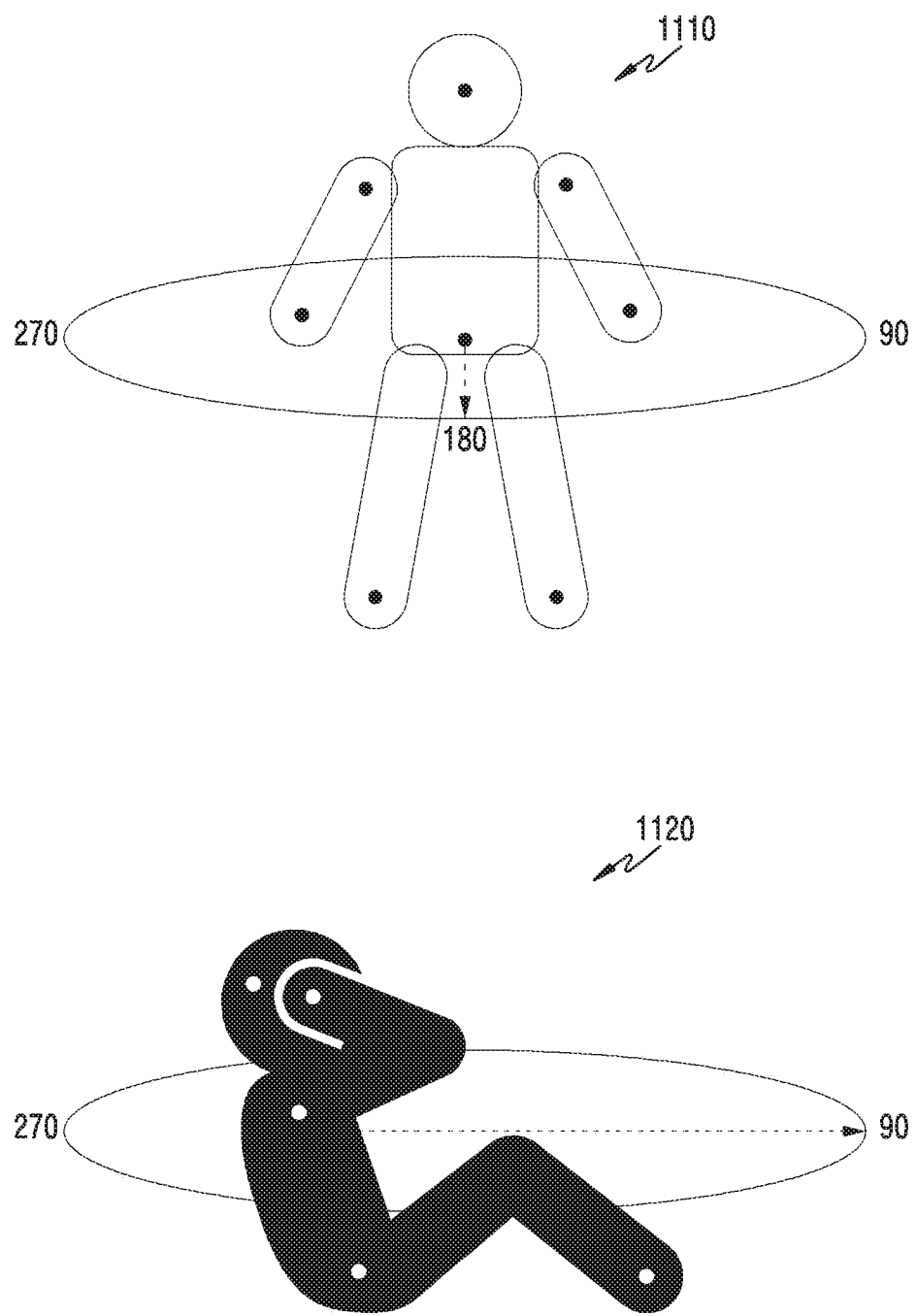
FIG. 11 illustrates a method of determining a target location of the electronic device according to an embodiment of the disclosure.

FIG. 10 is a flowchart 1000 illustrating a method by which the electronic device provides exercise guide information according to an embodiment of the disclosure, and FIG. 11 illustrates a method of determining a target location of the electronic device according to an embodiment of the disclosure.

Referring to FIGS. 10 and 11, an electronic device (for example, the electronic device 101 or the robot device 201) according to various embodiments of the disclosure may determine a target location (photographing location) using (by analyzing) a guide image. Operations 1001, 1003, and 1005 of FIG. 10 are similar to operations 401, 403, and 405 of FIG. 4, and thus a detailed description thereof is omitted.

The processor according to an embodiment of the disclosure may select a guide image corresponding to the selected exercise in operation 1007. The processor according to an embodiment of the disclosure may determine target posture information by analyzing the selected guide image in operation 1009. The target posture information may be used to predict a relative location of the device photographing the guide image. According to some embodiments, the target posture information may be received together with the guide image. For example, the target posture information may be embedded into a file of the guide image.

The processor according to an embodiment of the disclosure may acquire a user image (hereinafter, referred to as a first image) in operation 1011, and determine user posture information in operation 1013. For example, the processor (or the posture detection module 310) may determine the user in the first image acquired through the camera and determine user posture information.

Operations 1011 and 1013 may be performed almost simultaneously with operations 1007 and 1009 or performed sequentially.

The processor according to an embodiment of the disclosure may determine a target location on the basis of at least some of the target posture information and the user posture information in operation 1015. For example, when an azimuth (φ) which the user faces is 180 degrees as indicated by reference numeral 1110 of FIG. 11 and an azimuth (φ) which the person within the guide image faces is 90 degrees as indicated by reference numeral 1120, the processor (or the target location determination module 340) may determine a location moved by 90 degrees (=180−90) as a target location (hereinafter, referred to as a first target location).

According to some embodiments, the processor (or the target location determination module 340) may calculate a distance between the electronic device and the user such that an occupation ratio of the user in the user image becomes similar to an occupation ratio of the person in the guide image and determine a location moved by the calculated distance as a target location (hereinafter, referred to as a second target location).

When the target location is determined, the processor may perform operations 1017, 1019, and 1021. Operations 1017, 1019, and 1021 of FIG. 10 are similar to operations 417, 419, and 421 of FIG. 4. A detailed description thereof is omitted.

Figure 12:
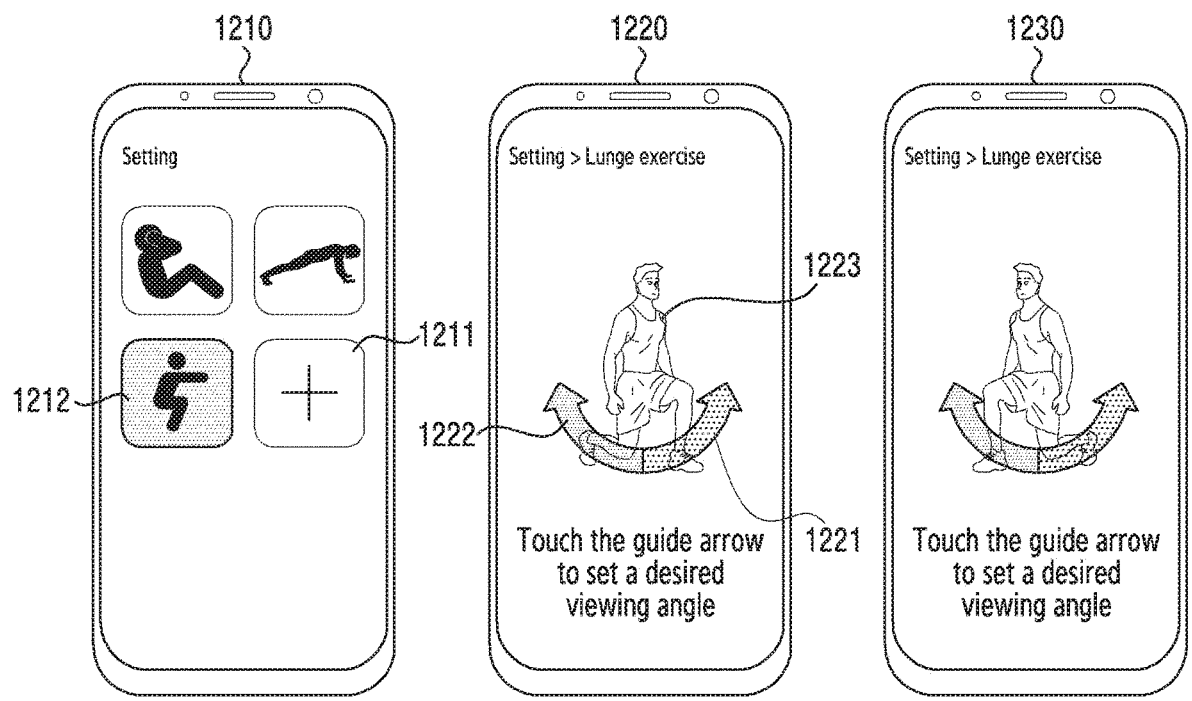
FIG. 12 illustrates an example of a screen on which a photographing location of a camera is set for each exercise according to an embodiment of the disclosure.

FIG. 12 illustrates an example of a screen on which a photographing location of a camera is set for each exercise according to an embodiment of the disclosure.

Referring to FIG. 12, an electronic device (for example, the electronic device 101 or the robot device 201) according to an embodiment of the disclosure may provide a user interface (hereinafter, referred to as a setting interface) for setting a photographing location of the camera for each exercise. For example, the setting interface may be provided through a display device (for example, the display device 160 or the output module 220) included in the electronic device, or a mobile terminal (for example, the mobile terminal 202) or an external device (for example, the external device 203) connected to the electronic device. Hereinafter, an example in which the setting interface is provided through the mobile terminal (for example, a smart phone) is described for convenience.

When a setting menu is activated (selected), the mobile terminal may output a first screen including a list of available exercises on the display (for example, a touch screen display) as indicated by reference numeral 1210. For example, the exercise list may include sit-up, pushup, and lunge exercises. The first screen may further include an additional menu 1211 on one side thereof.

When a specific exercise (for example, the lunge exercise 1212) is selected from the exercise list, the mobile terminal may output a second screen for setting a viewing angle of the camera (or a photographing direction or a photographing location of the camera) included in the electronic device on the display. The second screen may include a first indicator 1221 for moving the viewing angle to the right, a second indicator 1222 for moving the viewing angle to the left, and an image 1223 of a person taking a posture of the lunge exercise as indicated by reference numeral 1220.

The user may set a view angle of the camera included in the electronic device through the first indicator 1221 or the second indicator 1222. For example, upon receiving a user input for the first indicator 1221 or the second indicator 1222, the mobile terminal may rotate the image 1223 to the left or to the right. Whenever a user input is detected on the first indicator 1221, the mobile terminal may rotate the image 1223 displayed within the second screen in a counterclockwise direction by a predetermined size (for example, 5 degrees). Reference numeral 1230 of FIG. 12 indicates an example in which the image 1223 is rotates by 180 degrees.

According to some embodiments, the mobile terminal may rotate the image 1223 three-dimensionally (for example, in a yaw, pitch, or roll direction).

According to some embodiments, the second screen may be expressed in the form of a spherical coordinate system as indicated by reference numeral 620 of FIG. 6.

Figure 13:
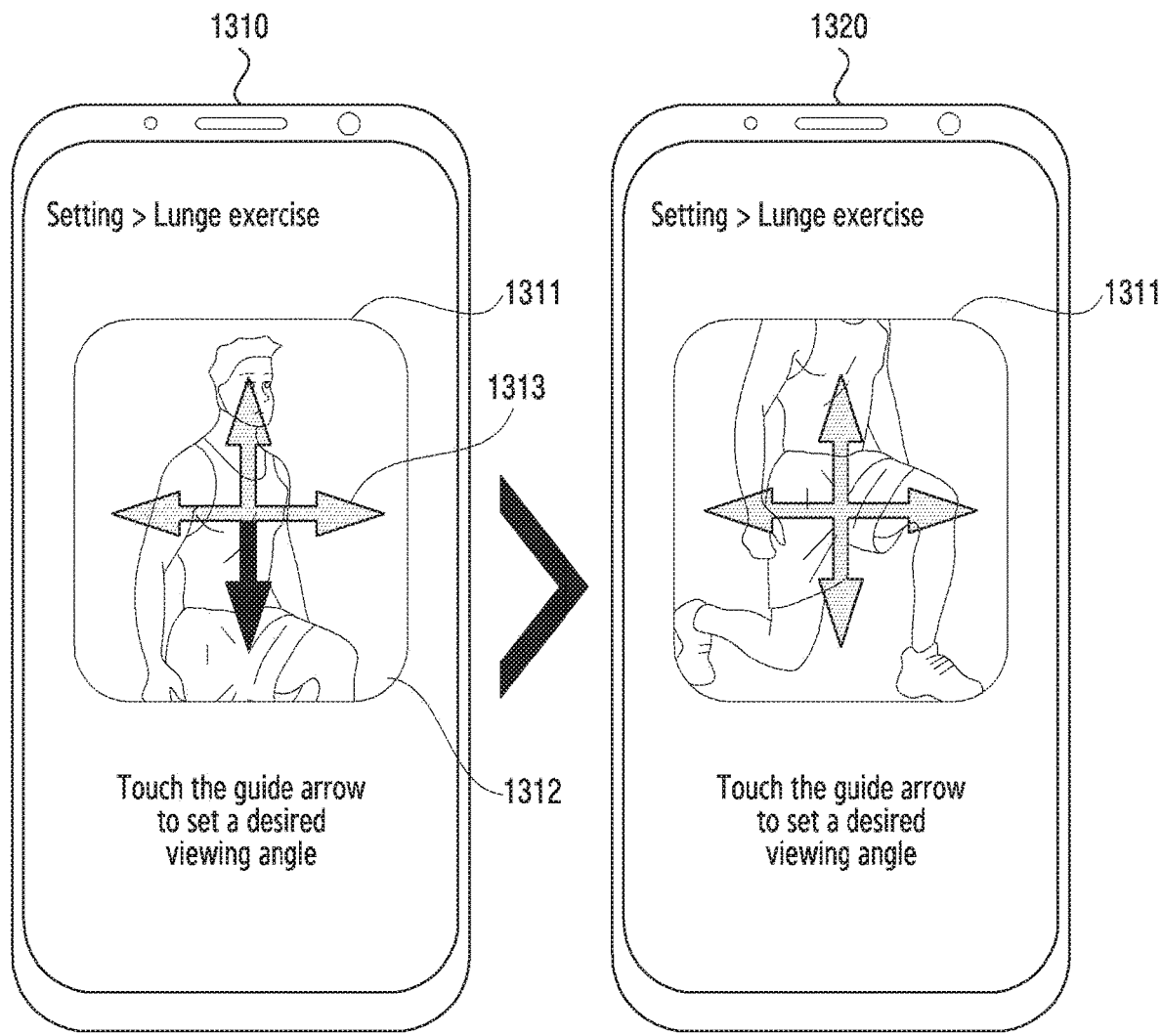
FIG. 13 illustrates an example of a screen on which a photographing location of a camera is set for each exercise according to an embodiment of the disclosure.

FIG. 13 illustrates an example of a screen on which a photographing location of a camera is set for each exercise according to an embodiment of the disclosure.

Referring to FIG. 13, according to an embodiment of the disclosure, an electronic device (for example, the electronic device 101 or the robot device 201) may be configured to photograph a body part of the user. This may be used when a distance between the electronic device and the user is not sufficiently secured. For example, a setting interface may include an image display area 1311 for displaying only a portion of a user image 1312 and a third indicator 1313 for scrolling the user image 1312 upward, downward, leftward, and rightward as indicated by reference numeral 1310.

When a downward scroll instruction is input through third indicator 1313, the mobile terminal may scroll the user image 1312 upward as indicated by reference numeral 1320. As described above, through the third indicator 1313, the user may select a body part to be photographed. Meanwhile, although not illustrated in FIG. 13, after selecting the body part, the user may rotate the selected body part three-dimensionally similarly to FIG. 12.

Figure 14:
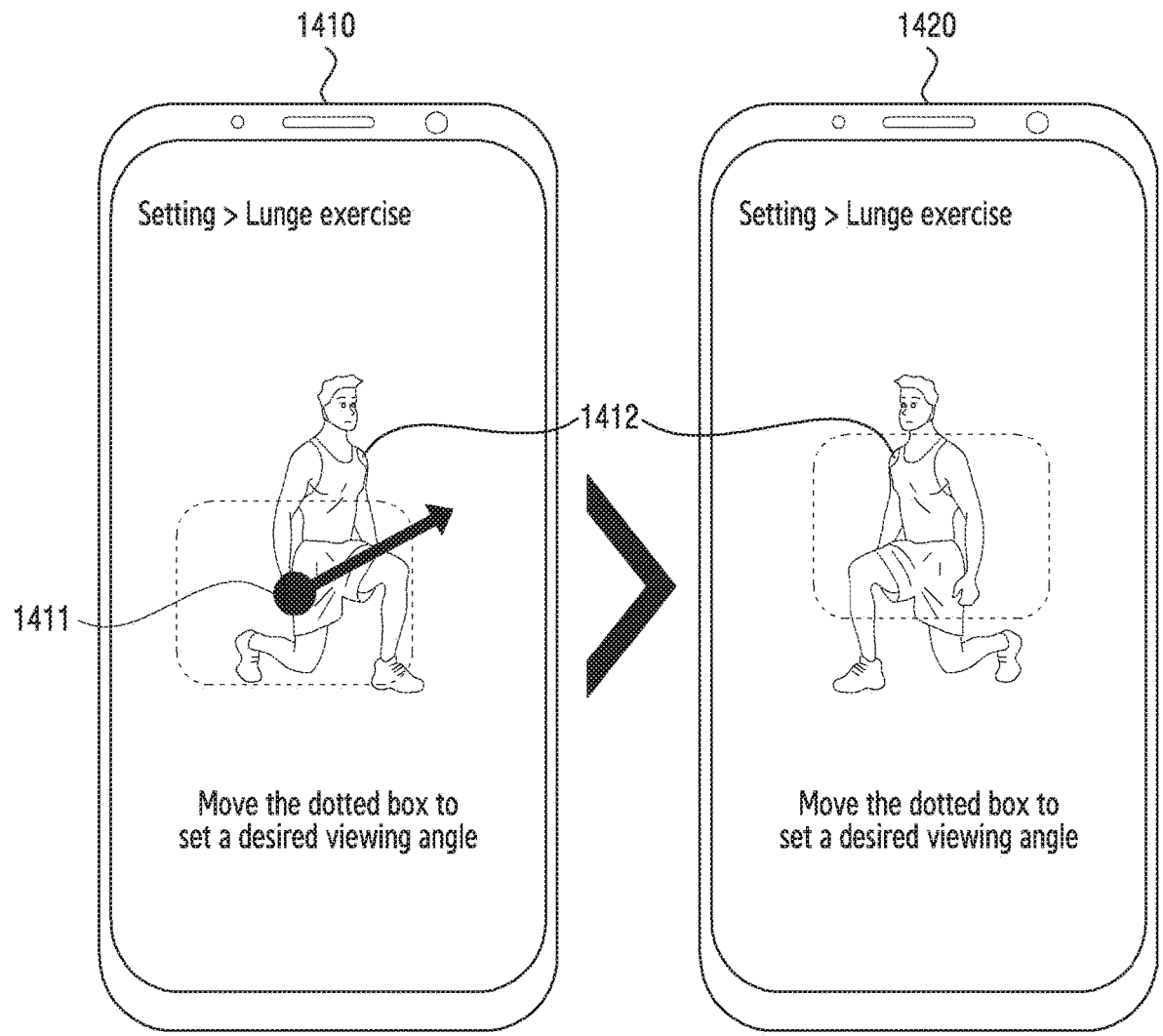
FIG. 14 illustrates an example of a screen on which a photographing location of a camera is set for each exercise according to an embodiment of the disclosure.

FIG. 14 illustrates an example of a screen on which a photographing location of a camera is set for each exercise according to an embodiment of the disclosure.

Referring to FIG. 14, an electronic device (for example, the electronic device 101 or the robot device 201) according to an embodiment of the disclosure may be configured to photograph a user body part. This may be used when a distance between the electronic device and the user is not sufficiently secured. For example, a setting interface may include a user image 1412 indicating whole feature of the user and a dotted box 1411 indicating a part to be photographed, as indicated by reference numeral 1410. The user may change the part to be photographed by moving the dotted box 1411 (for example, performing touch & drag on an edge of the dotted box 1411) as indicated by reference numeral 1420. Further, the user may rotate the user image 1412 in a similar way to or a different way (for example, touch the user image and then move the user image while touching the same) from FIG. 12.

According to some embodiments, the size of the dotted box 1411 may be changed within a maximum distance between the user and the electronic device.

Figure 15:
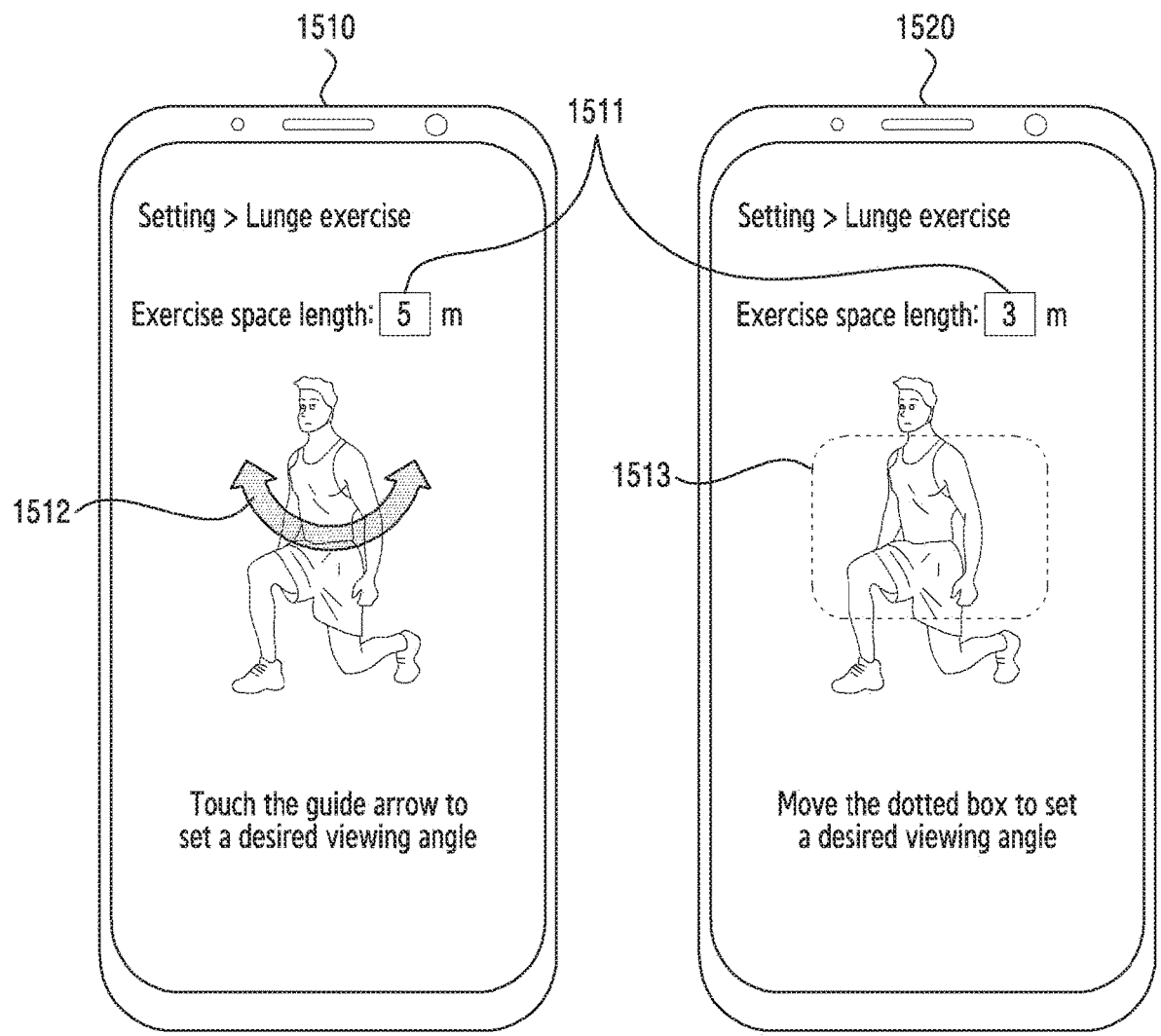
FIG. 15 illustrates an example of a screen on which a photographing location of a camera is set for each exercise according to an embodiment of the disclosure.

FIG. 15 illustrates an example of a screen on which a photographing location of a camera is set for each exercise according to an embodiment of the disclosure.

Referring to FIG. 15, an electronic device (for example, the electronic device 101 or the robot device 201) according to an embodiment of the disclosure may provide a setting interface in different forms according to the distance between the user and the electronic device. For example, the setting interface may include an input field 1511 into which the distance can be input, as illustrated in FIG. 15. The distance may be input into the input field 1511 by the user. According to some embodiments, the distance may be input by the electronic device. For example, the electronic device may predict the distance between the user and the electronic device in the current space (for example, living room) on the basis of the previously stored space map information and input the predicted distance into the input field 1511.

According to some embodiments, the distance predicted by the electronic device may be input into the input field as a default value and may be changed by the user.

When the value input into the input field 1511 is larger than or equal to a predetermined value (for example, a minimum distance at which the whole body of the user can be photographed), the electronic device may provide a user interface for setting a viewing angle through an indicator 1512, as indicated by reference numeral 1510. On the other hand, when the value input into the input field 1511 is smaller than the predetermined value, the electronic device may provide a user interface including a dotted box 1513 for setting a viewing angle to photograph a body part, as indicated by reference numeral 1520.

Figure 16:
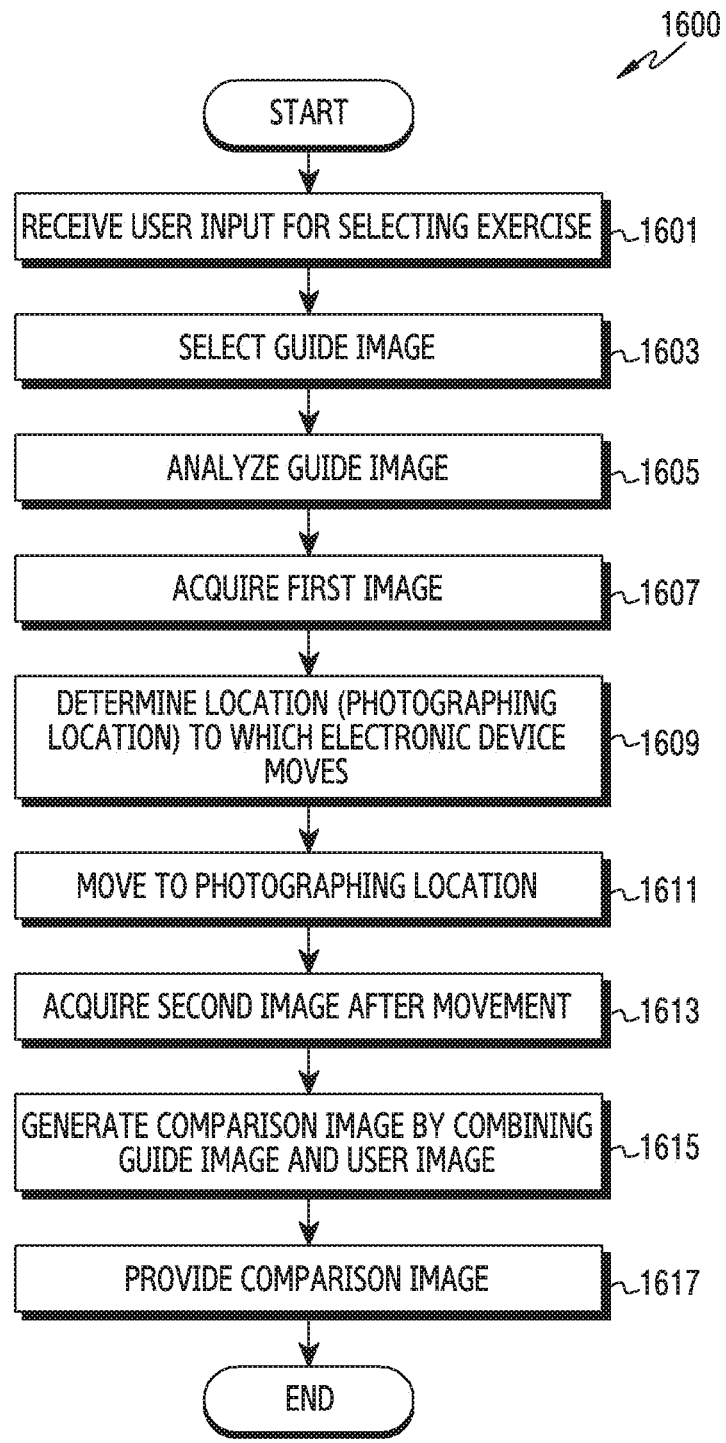
FIG. 16 is a flowchart illustrating a method by which the electronic device provides exercise guide information according to an embodiment of the disclosure.

FIG. 16 is a flowchart 1600 illustrating a method by which the electronic device provides exercise guide information according to an embodiment of the disclosure.

Prior to a detailed description, it is assumed that an electronic device (for example, the electronic device 101 or the robot device 201) executes an exercise guide application and is connected to an external device.

Referring to FIG. 16, a processor (for example, the processor 120) of the electronic device according to an embodiment of the disclosure may receive a user input for selecting an exercise in operation 1601. For example, the processor may receive a user input for selecting an exercise to be conducted, from an exercise list through a user interface or a wireless communication circuit.

The processor according to an embodiment of the disclosure may select a guide image corresponding to the selected exercise in operation 1603.

The processor according to an embodiment of the disclosure may analyze the guide image in operation 1605.

The processor according to an embodiment of the disclosure may acquire a first image of the user in operation 1607. For example, the processor may photograph the user through a camera (for example, the camera (the camera module 180 or the image sensor of the input sensor 210)).

The processor according to an embodiment of the disclosure may determine a location (a photographing location) to which the electronic device moves in operation 1609. For example, the processor may determine a location (photographing location) to which the electronic device moves on the basis of at least a portion of the analyzed guide image or the acquired first image of the user. For example, the processor may determine user posture information by analyzing the user image, determine a current photographing direction and location according to the user posture information, and when the current photographing direction and location are different from a predetermined photographing location, move the electronic device to the determined photographing location. Alternatively, the processor may determine target posture information by analyzing the guide image, determine user posture information by analyzing the user image, and determine a photographing location on the basis of at least some of the target posture information and the user posture information. Alternatively, the processor may determine a photographing location on the basis of at least some of the target posture information provided together with (for example, embedded into) the guide image and the user posture information acquired through analysis of the user image.

The processor according to an embodiment of the disclosure may move the electronic device to the determined photographing location in operation 1611. For example, the processor may move the electronic device to the determined location by controlling a driver (for example, the driver 230).

The processor according to an embodiment of the disclosure may acquire a second image of the user in operation 1613. For example, the processor may control the camera to acquire the second image of the user after movement.

The processor according to an embodiment of the disclosure may generate a comparison image by combining the guide image and the user image in operation 1615 and provide the comparison image in operation 1617. For example, the processor may output the comparison image through the user interface (or the display device) included in the electronic device or the external device connected to the electronic device.

Figure 17:
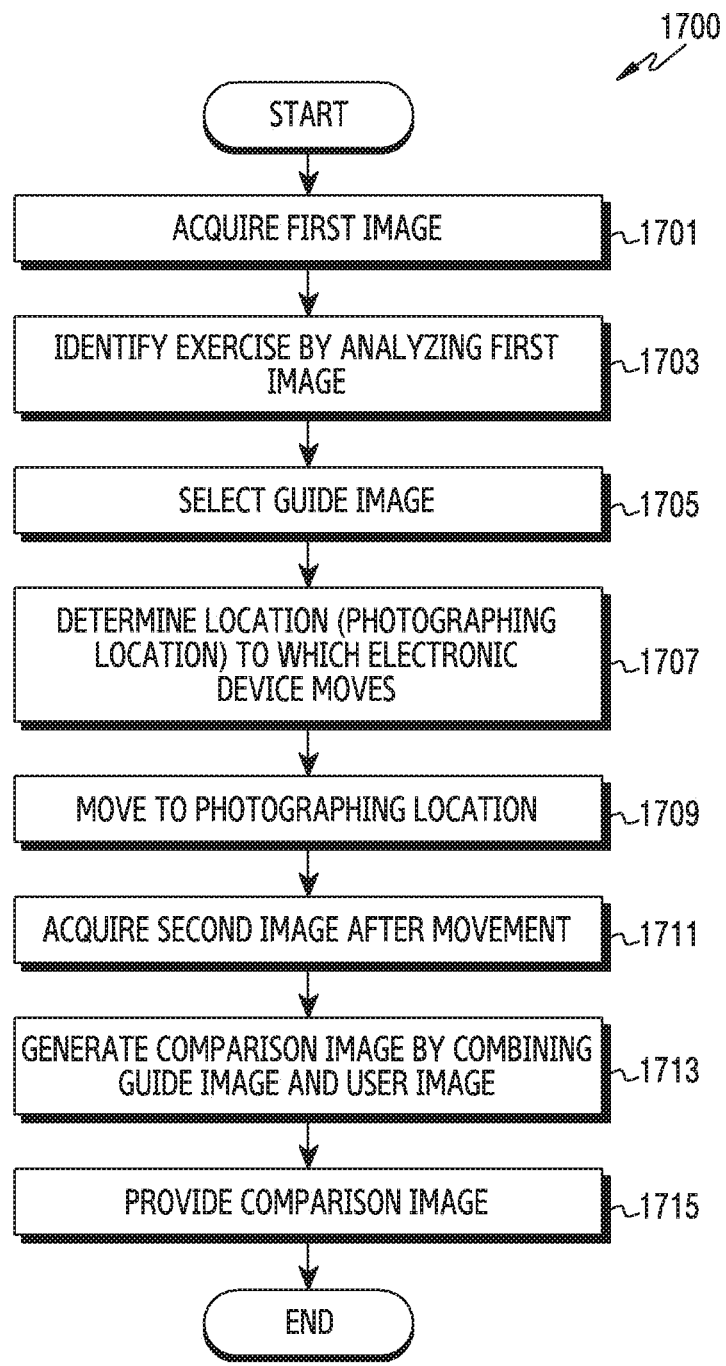
FIG. 17 is a flowchart illustrating a method by which the electronic device provides exercise guide information according to an embodiment of the disclosure.

FIG. 17 is a flowchart 1700 illustrating a method by which the electronic device provides exercise guide information according to an embodiment of the disclosure.

Prior to a detailed description, it is assumed that an electronic device (for example, the electronic device 101 or the robot device 201) executes an exercise guide application and is connected to an external device.

Referring to FIG. 17, a processor (for example, the processor 120) of the electronic device according to an embodiment of the disclosure may acquire a first image of the user in operation 1701. For example, the processor may photograph the user through a camera (for example, the image sensor of the camera (the camera module 180 or the image sensor of the input sensor 210).

The processor according to an embodiment of the disclosure may identify an exercise by analyzing the first image in operation 1703. For example, the processor may identify the type of the exercise which the user is doing by analyzing the first image through a classification algorithm (for example, a neural network, a CNN, an SVM, or a Bayes' classifier).

The processor according to an embodiment of the disclosure may select a guide image corresponding to the identified exercise in operation 1705.

The processor according to an embodiment of the disclosure may perform operations 1707, 1709, 1711, 1713, and 1715. Operations 1707, 1709, 1711, 1713, and 1715 are similar to operations 1609, 1611, 1613, 1615, and 1617 of FIG. 16, and thus a detailed description thereof is omitted.

According to various example embodiments of the disclosure, an electronic device (for example, the electronic device 101 or the robot device 201) may comprise: a housing; a user interface (for example, the display device 160, the output module 220, or the user interface 360); at least one camera (for example, the camera module 180 or the image sensor of the input sensor 210) disposed on the housing; at least one driver (for example, driver 230) connected to or disposed on the housing to move the housing; a wireless communication circuit (for example, the communication module 190 or the communication module 255) located within the housing; a memory (for example, the memory 130); and a processor (for example, the processor 120) operatively connected to the user interface, the at least one camera, the at least one driver, the wireless communication circuit, and the memory, wherein the memory stores instructions that, when executed by the processor, configure the processor to receive a user input for selecting an exercise through the user interface or the wireless communication circuit, select a guide image corresponding to the selected exercise, analyze the selected guide image, acquire a first image of a user through the at least one camera at a first location, determine a second location for the electronic device based at least in part on the analyzed guide image and the acquired first image of the user, control the at least one driver to move the electronic device based at least in part on the determined second location, acquire a second image of the user through the at least one camera after the move of the electronic device, and generate a combined image by combining the selected guide image and the acquired second image of the user.

According to various example embodiments, the memory may be configured to pre-store an exercise list including at least one exercise and at least one guide image corresponding to each of the at least one exercise, or wherein the instructions further configure the processor to download at least one of the exercise list or the at least one guide image from an external electronic device (for example, the server 108, or the content server 205) via the wireless communication circuit.

According to various example embodiments, the instructions may further configure the processor to display the combined image on the user interface or transmit the combined image to an external electronic device (for example, the electronic device 102, the mobile terminal 202, or the external device 203).

According to various example embodiments, the instructions may further configure the processor to acquire posture information of the user by analyzing the first image and determine the second location for the electronic device further based at least in part on relative location information set by the user and location information according to the acquired posture information of the user.

According to various example embodiments, the instructions may further configure the processor to extract target posture information embedded into the selected guide image, acquire posture information of the user by analyzing the first image, and determine the second location for the electronic device, further based at least in part on the extracted target posture information and the acquired posture information of the user.

According to various example embodiments, the instructions may further configure the processor to determine target posture information by analyzing the selected guide image, acquire posture information of the user by analyzing the first image, and determine the second location for the electronic device, further based at least in part on the determined target posture information and the acquired posture information of the user.

According to various example embodiments, the instructions may further configure the processor to determine a distance between the user and the electronic device, based at least in part on an occupation ratio of the user in the second image and determine the second location for the electronic device, based at least in part on the determined distance.

According to various example embodiments, the second location for the electronic device may be expressed by at least one of an azimuth, an angle of altitude, or a distance from a location of the user.

According to various example embodiments of the disclosure, an electronic device (for example, the electronic device 101 or the robot device 201) may comprise: a housing; a user interface (for example, the display device 160, the output module 220, or the user interface 360); at least one camera (for example, the camera module 180 or the image sensor of the input sensor 210) disposed on the housing; at least one driver (for example, driver 230) connected to or disposed on the housing to move the housing; a wireless communication circuit (for example, the communication module 190 or the communication module 255) located within the housing; a memory (for example, the memory 130); and a processor (for example, the processor 120) operatively connected to the user interface, the at least one camera, the at least one driver, the wireless communication circuit, and the memory, wherein the memory stores instructions that, when executed by the processor, configure the processor to acquire a first image of a user through the at least one camera at a first location, identify an exercise by analyzing the acquired first image, select a guide image corresponding to the identified exercise, determine a second location for the electronic device, based at least in part on the selected guide image and the acquired first image, control the at least one driver to move the electronic device, based at least in part on the determined second location, acquire a second image of the user through the at least one camera after a movement of the electronic device, and generate a combined image by combining the selected guide image and the acquired second image of the user.

According to various example embodiments, the memory may be configured to pre-store an exercise list including at least one exercise and at least one guide image corresponding to each of the at least one exercise, or wherein the instructions further configure the processor to download at least one of the exercise list or the at least one guide image from an external electronic device (for example, the server 108, or the content server 205) via the wireless communication circuit.

According to various example embodiments, the instructions may further configure the processor to display the combined image on the user interface or transmit the combined image to an external electronic device (for example, the electronic device 102, the mobile terminal 202, or the external device 203).

According to various example embodiments, the instructions may further configure the processor to acquire posture information of the user by analyzing the first image and determine the second location for the electronic device further based at least in part on relative location information set by the user and location information according to the acquired posture information of the user.

According to various example embodiments, the instructions may further configure the processor to determine target posture information by analyzing the selected guide image, acquire posture information of the user by analyzing the first image, and determine the second location for the electronic device further based at least in part on the determined target posture information and the acquired posture information of the user.

According to various example embodiments, the instructions may further configure the processor to extract target posture information embedded into the selected guide image, acquire posture information of the user by analyzing the first image, and determine the second location for the electronic device further based at least in part on the extracted target posture information and the acquired posture information of the user.

According to various example embodiments, the instructions may further configure the processor to determine a distance between the user and the electronic device, based at least in part on an occupation ratio of the user in the second image and determine the second location for the electronic device further based at least in part on the determined distance.

According to various example embodiments, the second location for the electronic device may be expressed by at least one of an azimuth, an angle of altitude, or a distance from a location of the user.

According to various example embodiments of the disclosure, an electronic device (for example, the electronic device 101 or the robot device 201) may comprise: a housing; a processor (for example, the processor 120); and a memory (for example, the memory 130) operatively connected to the processor, wherein the memory stores instructions that, when executed by the processor, configured the processor to determine a size of an exercise space, based at least in part on a stored space map, determine a type of a setting screen for setting a location or a direction of a camera, based at least in part on the determined size of the exercise space, and provide the determined type of the setting screen.

According to various example embodiments, the instructions may further configure the processor to modify the determined size of the exercise space according to a user input.

According to various example embodiments, the type of the setting screen may comprise one of a first type in which a viewing angle is set to photograph a body part of a user in a first set direction or a second type in which a viewing angle is set to photograph the whole body of the user in a second set direction.

According to various example embodiments, the instructions may further configure the processor to display the determined type of the setting screen on at least one of a display (for example, the display device 160, the output module 220) included in the electronic device or an external device (for example, the electronic device 102, the mobile terminal 202, or the external device 203) connected to the electronic device.

According to various example embodiments of the disclosure, a method for providing information of an electronic device (for example, the electronic device 101 or the robot device 201) may include an operation of receiving a user input for selecting an exercise through a user interface (for example, the display device 160, the output module 220, or the user interface 360) or a wireless communication circuit (for example, the communication module 190 or the communication module 255), an operation of selecting a guide image corresponding to the selected exercise, an operation of analyzing the selected guide image, an operation of acquiring a first image of a user through at least one camera at a first location (for example, the camera module 180 or the image sensor of the input sensor 210), an operation of determining a second location for the electronic device based at least in part on the analyzed guide image and the acquired first image of the user, an operation of controlling at least one driver to move the electronic device based at least in part on the determined second location, an operation of acquiring a second image of the user through the at least one camera after a movement of the electronic device, and an operation of generating a combined image by combining the selected guide image and the acquired second image of the user.

According to various embodiments, the method may further include at least one of an operation of pre-storing an exercise list including at least one exercise and at least one guide image corresponding to each of the at least one exercise in a memory (for example, the memory 130) or an operation of downloading at least one of the exercise list or the at least one guide image from an external electronic device (for example, the server 108 or the content server 205).

According to various embodiments, the method may further include an operation of displaying the combined image on the user interface or transmitting the combined image to an external electronic device.

According to various embodiments, the operation of determining the second location for the electronic device may include an operation of acquiring posture information of the user by analyzing the first image and an operation of determining the second location for the electronic device further based at least in part on relative location information set by the user and location information according to the acquired posture information of the user.

According to various embodiments, the operation of determining the second location for the electronic device may include an operation of extracting target posture information embedded into the selected guide image, an operation of acquiring posture information of the user by analyzing the first image, and an operation of determining the second location for the electronic device further based at least in part on the extracted target posture information and the acquired posture information of the user.

According to various embodiments, the operation of determining the second location for the electronic device moves may include an operation of determining target posture information by analyzing the selected guide image, an operation of acquiring posture information of the user by analyzing the first image, and an operation of determining the second location for the electronic device further based at least in part on the determined target posture information and the acquired posture information of the user.

According to various embodiments, the operation of determining the second location for the electronic device may include an operation of determining a distance between the user and the electronic device based at least in part on an occupation ratio of the user in the second image and an operation of determining the second location for the electronic device further based at least in part on the determined distance.

According to various embodiments, the second location for the electronic device may be expressed by at least one of an azimuth, an angle of altitude, or a distance from a location of the user.

According to various example embodiments of the disclosure, a method for providing information of an electronic device (for example, the electronic device 101 or the robot device 201) may include an operation of acquiring a first image of a user through at least one camera at a first location (for example, the camera module 180 or the image sensor of the input sensor 210), an operation of identifying an exercise by analyzing the acquired first image, operation of selecting a guide image corresponding to the identified exercise, operation of determining a second location for the electronic device based at least in part on the selected guide image and the acquired first image, operation of controlling at least one driver (for example, the driver 230) to move the electronic device based at least in part on the determined second location, operation of acquiring a second image of the user through the at least one camera after a movement of the electronic device, and operation of generating a combined image by combining the selected guide image and the acquired second image of the user.

According to various embodiments, the method may further include at least one of an operation of pre-storing an exercise list including at least one exercise and at least one guide image corresponding to each of the at least one exercise in a memory (for example, the memory 130); or an operation of downloading at least one of the exercise list or the at least one guide image from an external electronic device (for example, the server 108 or the content server 205).

According to various embodiments, the method may further include an operation of displaying the combined image on a user interface (for example, the display device 160, the output module 220, or the user interface 360) or transmitting the combined image to an external electronic device (for example, the electronic device 102, the mobile terminal 202, or the external device 203).

According to various embodiments, the operation of determining the second location for the electronic device may include an operation of acquiring posture information of the user by analyzing the first image and an operation of determining the second location for the electronic device further based at least in part on relative location information set by the user and location information according to the acquired posture information of the user.

According to various embodiments, the operation of determining the second location for the electronic device may include an operation of determining target posture information by analyzing the selected guide image, an operation of acquiring posture information of the user by analyzing the first image, and an operation of determining the second location for the electronic device further based at least in part on the determined target posture information and the acquired posture information of the user.

According to various embodiments, the operation of determining the second location for the electronic device may include an operation of extracting target posture information embedded into the selected guide image, an operation of acquiring posture information of the user by analyzing the first image, and an operation of determining the second location for the electronic device further based at least in part on the extracted target posture information and the acquired posture information of the user.

According to various embodiments, the operation of determining the second location for the electronic device may include an operation of determining a distance between the user and the electronic device based at least in part on an occupation ratio of the user in the second image and an operation of determining the second location the electronic device further based at least in part on the determined distance.

According to various embodiments, the second location for the electronic device may be expressed by at least one of an azimuth, an angle of altitude, or a distance from a location of the user.

According to various example embodiments of the disclosure, a method for providing information of an electronic device (for example, the electronic device 101 or the robot device 201) may include an operation of determining a size of an exercise space based at least in part on a stored space map, an operation of determining a type of a setting screen for setting a location or a direction of a camera based at least in part on the determined size of the exercise space, and an operation of displaying the determined type of the setting screen on a display (for example, the display device 160, the output module 220, or the user interface 360).

According to various embodiments, the method may further include an operation of modifying the determined size of the exercise space according to a user input.

According to various embodiments, the type of the setting screen may include one of a first type in which a viewing angle is set to photograph a body part of a user in a first set direction or a second type in which a viewing angle is set to photograph the whole body of the user in a second set direction.

According to various embodiments, the operation of displaying the determined type of the setting screen may include at least one of an operation of displaying the determined type of the setting screen on at least one of the display or an operation of transmitting the determined type of the setting screen to an external electronic device (for example, the electronic device 102, the mobile terminal 202, or the external device 203) connected to the electronic device and displaying the same.

The electronic device may move to a location designated for each exercise or a location selected on the basis of a guide image of a selected exercise, photograph a user feature, and output a photographed image to an external device (for example, a TV or a beam projector). The user may easily identify an exercise posture photographed at a desired location. Further, the electronic device may output the photographed image and the guide image together. Accordingly, the user may easily identify whether his/her posture is correct.

According to various embodiments of the disclosure, it is possible to photograph a user at a designated (or set) location or a determined location according to an exercise (a relative location based on the user) and easily identify the photographed user feature. According to various embodiments of the disclosure, even though the user moves, the electronic device may move to a designated location or a determined location and thus photograph the user, thereby improving user convenience. Various embodiments of the disclosure may provide the user image and the guide image together. Accordingly, the user may easily identify whether an exercise posture is correct.

The electronic device according to various example embodiments may be one of various types of electronic devices. The electronic devices may include, for example, and without limitation, a portable communication device (e.g., a smartphone), a computer device, a portable multimedia device, a portable medical device, a camera, a wearable device, a home appliance, or the like. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., wiredly), wirelessly, or via a third element.

As used herein, the term "module" may include a unit implemented in hardware, software, or firmware, or any combination thereof and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the disclosure has been illustrated and described with reference to various embodiments thereof, it will be understood by those skilled in the art that various changes in form and details may be made therein without departing from the spirit and scope of the disclosure, as defined by the appended claims and their equivalents.

What is claimed is:

1. An electronic device comprising:
   a housing;
   a user interface;
   at least one camera disposed on the housing;
   at least one driver connected to or disposed on the housing to move the housing;
   a wireless communication circuit located within the housing;
   a memory; and
   a processor operatively connected to the user interface, the at least one camera, the at least one driver, the wireless communication circuit, and the memory,
   wherein the memory stores instructions that, when executed by the processor, configure the processor to:
      receive a user input for selecting an exercise through the user interface or the wireless communication circuit,
      select a guide image corresponding to the selected exercise,
      analyze the selected guide image,
      acquire a first image of a user through the at least one camera at a first location,
      determine a second location for the electronic device, based at least in part on the analyzed guide image and the acquired first image of the user,
      control the at least one driver to move the electronic device, based at least in part on the determined second location,
      acquire a second image of the user through the at least one camera after a movement of the electronic device, and
      generate a combined image by combining the selected guide image and the acquired second image of the user.

2. The electronic device of claim 1,
   wherein the memory is configured to pre-store an exercise list including at least one exercise and at least one guide image corresponding to each of the at least one exercise, or
   wherein the instructions further configure the processor to download at least one of the exercise list or the at least one guide image from an external electronic device via the wireless communication circuit.

3. The electronic device of claim 1, wherein the instructions further configure the processor to display the combined image on the user interface or transmit the combined image to an external electronic device.

4. The electronic device of claim 1, wherein the instructions further configure the processor to:
   acquire posture information of the user by analyzing the first image, and
   determine the second location for the electronic device further based at least in part on relative location information set by the user and the acquired posture information of the user.

5. The electronic device of claim 1, wherein the instructions further configure the processor to:
   extract target posture information embedded into the selected guide image,
   acquire posture information of the user by analyzing the first image, and
   determine the second location for the electronic device further based at least in part on the extracted target posture information and the acquired posture information of the user.

6. The electronic device of claim 1, wherein the instructions further configure the processor to:
   determine target posture information by analyzing the selected guide image,
   acquire posture information of the user by analyzing the first image, and
   determine the second location for the electronic device further based at least in part on the determined target posture information and the acquired posture information of the user.

7. The electronic device of claim 1, wherein the instructions further configure the processor to:
   determine a distance between the user and the electronic device, based at least in part on an occupation ratio of the user in the second image, and
   determine the second location for the electronic device, based at least in part on the determined distance.

8. The electronic device of claim 1, wherein the second location for the electronic device is expressed by at least one of an azimuth, an angle of altitude, or a distance from a location of the user.

9. An electronic device comprising:
   a housing;
   a user interface;
   at least one camera disposed on the housing;
   at least one driver connected to or disposed on the housing to move the housing;

a wireless communication circuit located within the housing;

a memory; and a processor operatively connected to the user interface, the at least one camera, the at least one driver, the wireless communication circuit, and the memory, wherein the memory stores instructions that, when executed by the processor, configure the processor to:

acquire a first image of a user through the at least one camera at a first location, identify an exercise by analyzing the acquired first image, select a guide image corresponding to the identified exercise, determine a second location for the electronic device, based at least in part on the selected guide image and the acquired first image, control the at least one driver to move the electronic device, based at least in part on the determined second location, acquire a second image of the user through the at least one camera after a movement of the electronic device, and generate a combined image by combining the selected guide image and the acquired second image of the user.

10. The electronic device of claim 9, wherein the memory is configured to pre-store an exercise list including at least one exercise and at least one guide image corresponding to each of the at least one exercise, or wherein the instructions further configure the processor to download at least one of the exercise list or the at least one guide image from an external electronic device via the wireless communication circuit.

11. The electronic device of claim 9, wherein the instructions further configure the processor to display the combined image on the user interface or transmit the combined image to an external electronic device.

12. The electronic device of claim 9, wherein the instructions further configure the processor to:

acquire posture information of the user by analyzing the first image, and determine the second location for the electronic device further based at least in part on relative location information set by the user and the acquired posture information of the user.

13. The electronic device of claim 9, wherein the instructions further configure the processor to:

determine target posture information by analyzing the selected guide image, acquire posture information of the user by analyzing the first image, and determine the second location for the electronic device further based at least in part on the determined target posture information and the acquired posture information of the user.

14. The electronic device of claim 9, wherein the instructions further configure the processor to:

extract target posture information embedded into the selected guide image, acquire posture information of the user by analyzing the first image, and determine the second location for the electronic device further based at least in part on the extracted target posture information and the acquired posture information of the user.

15. The electronic device of claim 9, wherein the instructions further configure the processor to:

determine a distance between the user and the electronic device, based at least in part on an occupation ratio of the user in the second image, and determine the second location for the electronic device, based at least in part on the determined distance.

16. The electronic device of claim 9, wherein the second location for the electronic device is expressed by at least one of an azimuth, an angle of altitude, or a distance from a location of the user.

* * * * *